US008288391B2

(12) United States Patent
Johnson et al.

(10) Patent No.: US 8,288,391 B2
(45) Date of Patent: Oct. 16, 2012

(54) PYRAZINOYLGUANIDINE COMPOUNDS FOR USE AS TASTE MODULATORS

(75) Inventors: Michael R. Johnson, Chapel Hill, NC (US); Richard C. Boucher, Chapel Hill, NC (US); Andrew J. Hirsh, Durham, NC (US)

(73) Assignee: Parion Sciences, Inc., Durham, NC (US)

( * ) Notice: Subject to any disclaimer, the term of this patent is extended or adjusted under 35 U.S.C. 154(b) by 328 days.

(21) Appl. No.: 12/061,864

(22) Filed: Apr. 3, 2008

(65) Prior Publication Data
US 2008/0249109 A1    Oct. 9, 2008

Related U.S. Application Data

(60) Provisional application No. 60/909,818, filed on Apr. 3, 2007.

(51) Int. Cl.
A61K 31/4965     (2006.01)
(52) U.S. Cl. .................................. 514/255.06
(58) Field of Classification Search .................. None
See application file for complete search history.

(56) References Cited

U.S. PATENT DOCUMENTS

| 6,858,614 | B2 | 2/2005 | Johnson |
| 6,858,615 | B2 | 2/2005 | Johnson |
| 6,903,105 | B2 | 6/2005 | Johnson |
| 6,995,160 | B2 | 2/2006 | Johnson |
| 7,026,325 | B2 | 4/2006 | Johnson |
| 7,030,117 | B2 | 4/2006 | Johnson |
| 7,064,129 | B2 | 6/2006 | Johnson |
| 7,186,833 | B2 | 3/2007 | Johnson |
| 7,189,719 | B2 | 3/2007 | Johnson |
| 7,192,958 | B2 | 3/2007 | Johnson |
| 7,192,959 | B2 | 3/2007 | Johnson |
| 7,192,960 | B2 | 3/2007 | Johnson |
| 7,241,766 | B2 | 7/2007 | Johnson |
| 7,247,636 | B2 | 7/2007 | Johnson |
| 7,247,637 | B2 | 7/2007 | Johnson et al. |
| 7,317,013 | B2 | 1/2008 | Johnson |
| 7,332,496 | B2 | 2/2008 | Johnson |
| 7,345,044 | B2 | 3/2008 | Johnson |
| 7,368,447 | B2 | 5/2008 | Johnson et al. |
| 7,368,450 | B2 | 5/2008 | Johnson |
| 7,368,451 | B2 | 5/2008 | Johnson et al. |
| 2003/0077369 | A1 | 4/2003 | Jager et al. |
| 2005/0080092 | A1 | 4/2005 | Johnson |
| 2005/0080093 | A1 | 4/2005 | Johnson et al. |
| 2005/0090505 | A1 | 4/2005 | Johnson et al. |
| 2005/0228182 | A1 | 10/2005 | Johnson et al. |
| 2006/0040954 | A1 | 2/2006 | Johnson |
| 2006/0068071 | A1 | 3/2006 | Dewis et al. |
| 2006/0142306 | A1 | 6/2006 | Johnson |
| 2006/0142581 | A1 | 6/2006 | Johnson |
| 2006/0205738 | A1 | 9/2006 | Johnson et al. |
| 2007/0021439 | A1 | 1/2007 | Johnson |
| 2007/0032509 | A1 | 2/2007 | Johnson et al. |
| 2007/0265280 | A1 | 11/2007 | Johnson |
| 2008/0076782 | A1 | 3/2008 | Johnson |
| 2008/0090841 | A1 | 4/2008 | Johnson et al. |
| 2008/0096896 | A1 | 4/2008 | Johnson |
| 2008/0103148 | A1 | 5/2008 | Johnson |

FOREIGN PATENT DOCUMENTS
WO    WO 2005/006881 A2    1/2005

OTHER PUBLICATIONS

Itoh et al., Circulation (1986), 59:342-347.*
Vippagunta et al., Advanced Drug Delivery Reviews, 48 (2001), pp. 3-26.*
Schiffman et al., Physiology & Behavior, (Mar. 1990), 47(3), pp. 435-441.*
U.S. Appl. No. 12/393,252, filed Feb. 26, 2009, Johnson.
U.S. Appl. No. 12/249,175, filed Oct. 10, 2008, Boucher, et al.
U.S. Appl. No. 12/304,006, filed Dec. 9, 2008, Johnson, et al.
U.S. Appl. No. 12/304,042, filed Dec. 9, 2008, Johnson.
U.S. Appl. No. 12/304,040, filed Dec. 9, 2008, Johnson.
U.S. Appl. No. 10/920,527, filed Aug. 18, 2004, Hopkins.
U.S. Appl. No. 11/573,413, filed Feb. 8, 2007, Johnson.
U.S. Appl. No. 11/573,421, filed Feb. 8, 2007, Johnson.
U.S. Appl. No. 11/696,003, filed Apr. 3, 2007, Johnson.
U.S. Appl. No. 11/852,003, filed Sep. 7, 2007, Johnson, et al.
U.S. Appl. No. 11/835,902, filed Aug. 8, 2007, Johnson, et al.
U.S. Appl. No. 12/049,946, filed Mar. 17, 2008, Johnson, et al.
U.S. Appl. No. 12/049,968, filed Mar. 17, 2008, Johnson, et al.
U.S. Appl. No. 12/049,894, filed Mar. 17, 2008, Johnson, et al.
U.S. Appl. No. 12/050,010, filed Mar. 17, 2008, Johnson.
U.S. Appl. No. 12/049,993, filed Mar. 17, 2008, Johnson.
U.S. Appl. No. 12/050,019, filed Mar. 17, 2008, Johnson.
U.S. Appl. No. 12/061,837, filed Apr. 3, 2008, Johnson, et al.
U.S. Appl. No. 12/098,581, filed Apr. 7, 2008, Johnson.
Corinne A. Ossebaard, et al., "Effect of Amiloride on the Taste of NaCl, Na-gluconate and KCl in Humans: Implications for Na+ Receptor Mechanisms", Chemical Senses, vol. 20, 1995, pp. 1-4.
U.S. Appl. No. 60/495,725, filed Aug. 18, 2003, Johnson.
U.S. Appl. No. 60/495,720, filed Aug. 18, 2003, Johnson.
U.S. Appl. No. 60/495,712, filed Aug. 18, 2003, Johnson.
U.S. Appl. No. 60/602,312, filed Aug. 18, 2004, Johnson.
U.S. Appl. No. 60/602,327, filed Aug. 18, 2004, Johnson.
U.S. Appl. No. 60/812,091, filed Jun. 9, 2006, Johnson.
U.S. Appl. No. 60/812,077, filed Jun. 9, 2006, Johnson, et al.
U.S. Appl. No. 60/812,078, filed Jun. 9, 2006, Johnson.
U.S. Appl. No. 60/842,669, filed Sep. 7, 2006, Johnson, et al.
U.S. Appl. No. 60/842,963, filed Sep. 8, 2006, Johnson, et al.
U.S. Appl. No. 60/845,171, filed Sep. 18, 2006, Johnson, et al.
U.S. Appl. No. 60/909,818, filed Apr. 3, 2007, Johnson, et al.
U.S. Appl. No. 60/978,887, filed Oct. 10, 2007, Boucher, et al.
U.S. Appl. No. 60/978,874, filed Oct. 10, 2007, Boucher, et al.
U.S. Appl. No. 60/987,663, filed Nov. 13, 2007, Johnson, et al.
U.S. Appl. No. 61/013,387, filed Dec. 13, 2007, Johnson, et al.
U.S. Appl. No. 61/030,313, filed Feb. 21, 2008, Johnson.

(Continued)

Primary Examiner — Phyllis G. Spivack
(74) Attorney, Agent, or Firm — Oblon, Spivak, McClelland, Maier & Neustadt, L.L.P.

(57) ABSTRACT

The present invention relates to blocking salt taste using compounds of Formula I as defined herein.

4 Claims, No Drawings

OTHER PUBLICATIONS

U.S. Appl. No. 61/031,466, filed Feb. 26, 2008, Johnson.
U.S. Appl. No. 12/171,814, filed Jul. 11, 2008, Johnson. et al.
U.S. Appl. No. 12/171,867, filed Jul. 11, 2008, Johnson. et al.
U.S. Appl. No. 12/171,897, filed Jul. 11, 2008, Johnson. et al.
U.S. Appl. No. 12/190,022, filed Aug. 12, 2008, Johnson.
U.S. Appl. No. 61/079,989, filed Jul. 11, 2008, Boucher, et al.
U.S. Appl. No. 12/179,353, filed Jul. 24, 2008, Johnson.
U.S. Appl. No. 60/909,802, filed Apr. 3, 2007, Johnson, et al.
U.S. Appl. No. 12/501,654, filed Jul. 13, 2009, Boucher, et al.

* cited by examiner

PYRAZINOYLGUANIDINE COMPOUNDS FOR USE AS TASTE MODULATORS

CONTINUING APPLICATION DATA

This application claims priority to U.S. application Ser. No. 60/909,818, filed on Apr. 3, 2007, and incorporated herein by reference in its entirety.

BACKGROUND OF THE INVENTION

1. Field of the Invention

The present invention relates to taste enhancers and taste attenuators. The present invention provides a variety of uses for a series of sodium channel blocking pyrazinoylguanidine compounds represented by formula (I) defined herein to modify the taste of various foodstuffs on the palate. These compounds can be used as taste modifiers in various foodstuffs.

2. Description of the Background

Humans, as a living organism, require nutrition like any other organism. As such, they also require a way to distinguish between safe food items and dangerous food items. This ability has evolved within us as a species, and it has resulted in the pleasure and displeasure we feel when eating certain foods. Bitter and sour foods that we find unpleasant, while salty, sweet, and meaty tasting foods generally provide a pleasurable sensation. The five specific tastes received by gustatory receptors are salt, sweet, bitter, sour, and umami, which means "savory" in Japanese. Both salt and sour taste mechanisms detect the presence of sodium chloride in the mouth in different ways. The detection of salt is important to many organisms, but specifically mammals, as it serves a critical role in ion and water homeostasis in the body. Because of this adaptive nature, salt elicits a pleasant response in most humans. Sour taste can be mildly pleasant in small quantities, as it is linked to the salt flavour, but in larger quantities it becomes more and more unpleasant to taste. This is because increasing sour taste can signal over-ripe fruit, rotten meat, and other spoiled foods, which can be dangerous to the body because of bacteria which grow in such mediums. As well, producing a sour taste, acids ($H^+$ ions) cause serious tissue damage. The bitter taste is almost completely unpleasant to humans.

Arguably the simplest receptor found in the mouth is the salt (NaCl) receptor. An ion channel in the taste cell wall allows $Na^+$ ions to enter the cell. This ion flow depolarizes the cell, and opens voltage-regulated $Ca^{2+}$ gates, flooding the cell with $Ca^{2+}$ ions and leading to neurotransmitter release. This sodium channel is known as ENaC (Epithelial Sodium Channel) and is composed of three subunits. ENaC can be blocked by the drug amiloride in many mammals including humans. The sensitivity of the salt taste to amiloride in humans, however, is less pronounced, leading to conjecture that there may be additional receptor proteins besides ENAC that may not have been discovered yet.

Sodium Taste and ENaC Pharmacology $Na^+$ transport across epithelia, including lingual epithelia, involves the passive flux of $Na^+$ from the luminal compartment (oral cavity for dorsal lingual epithelia) into the epithelial cells (for taste, receptor cells in taste buds and some surrounding non-taste epithelia) through apical membrane ENaC. $Na^+$ is then pumped across the basolateral membranes of the epithelial cells by the $Na^+$—$K^+$-ATPase (Verrey et al. (2000)). Transcelluar $Na^+$ transport can be inhibited at the cell apical membrane by adding amiloride or one of its analogues to the luminal solution, thereby reducing the $Na^+$ permeability of ENaC (Verrey et al. (2000)). For the species in which transepithelial ion transport has been studied across the dorsal lingual epithelium, viz., dog (DeSimone et al. (1984); Simon and Garvin (1985), Mierson et al. (1985)), rat (Heck et al. (1984); Mierson et al. (1988); Garvin et al. (1988); Gilbertson and Zhang (1998)), rabbit (Simon et al. (1986)) and hamster (Gilbertson and Zhang (1998)) the trans epithealial $Na^+$ transport paradigm appears to apply. The most compelling evidence that ENaC or some ENaC variants are indeed $Na^+$-specific salt taste receptor proteins is that the taste nerve response to NaCl is significantly inhibited by amiloride and its analogues in a variety of species. Taste responses to NaCl recorded in the afferent chorda tympani or in the nucleus of the solitary tract of rat (Schiffman et al. (1983); Heck et al. (1984); Brand et al. (1985); Hill and Bour (1985); Scott and Giza (1990); Yoshii et al. (1986); Ninomiya and Funakoshi (1988); St. John and Smith (2000)), hamster (Hettinger and Frank (1990)); some mouse strains (Ninomiya et al. (1989)), and gerbil (Schiffman et al. (1990)) are significantly inhibited by amiloride without effect on responses to stimuli of other taste modalities. Amiloride sensitivity is observed in single chorda tympani units of the chimpanzee that respond strongly to $Na^+$ and $L^+$ salts, but not in units sensitive to both $Na^+$ and $K^+$ (Hellekant et al. (1997)). Whole cell patch clamp studies on isolated rat and hamster taste buds show that amiloride blocks a $Na^+$ current across taste cell membranes, consistent with a role for ENaC in $Na^+$ taste reception (Avenet and Lindemann (1988; 1991); Gilbertson et al. (1992)). Taken together the data are consistent with the conclusion that ENaC is the $Na^+$ specific salt taste receptor in many species including many rodents and non-human primates. In rats the amiloride-sensitive part of the response accounts for 75%-80% of the total response to 100 mM NaCl. ENaC likely plays a role in the more complex mechanism of human salt taste (1995)).

Sour taste signals the presence of acidic compounds ($H^+$ ions in solution). There are three different receptor proteins at work in sour taste. The first is a simple ion channel which allows hydrogen ions to flow directly into the cell. The protein for this is ENaC, the same protein involved in the distinction of salt taste (this implies a relationship between salt and sour receptors and could explain why salty taste is reduced when a sour taste is present). There are also $H^+$ regulated channels present which are regulated by acid-sensing ion channels (ASIC's).

SUMMARY OF THE INVENTION

It is an object of the present invention to use epithelial sodium channel (ENaC) blockers that block the taste sensation associated with salt.

It is also an object of the present invention to use ASIC blockers that block the taste sensation associated with sour.

It is another object of the present invention to use sodium channel agonists to enhance the salt taste of low sodium foods.

It is the object of the present invention to provide uses that take advantage of the pharmacological properties of the compounds described above.

The invention also relates to a food composition comprising a food and a compound of Formula I as defined herein.

The invention also relates to administering or mixing a compound of Formula I as defined herein in a taste effective amount sufficient to modify sweetness, saltiness, bitter, sour or umami taste characteristics of the food.

The invention also relates to foods for addition a compound of Formula I as defined herein where such foods include chocolate, ice-cream, a beverage, a sugar confectionery, a culinary product, or a pet food.

The object of masking salt and sour taste in the present invention may be accomplished with a class of pyrazinoylguanidine compounds represented by formula (I):

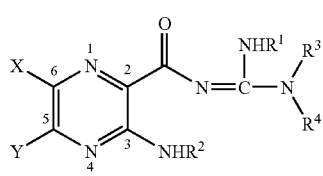

wherein the definition of these compounds and the parameters of $R^1$, $R^2$, $R^3$, $R^4$, X any Y are found in the variously defined pyrazinoylguanidine compounds of Formula I described in U.S. Pat. No. 6,858,614, Feb. 22, 2005; U.S. Pat. No. 6,858,615, Feb. 22, 2005, U.S. Pat. No. 6,903,105, Jun. 7, 2005; U.S. Pat. No. 6,995,160, Feb. 7, 2006; U.S. Pat. No. 7,026,325, Apr. 11, 2006; U.S. Pat. No. 7,030,117, Apr. 18, 2006; U.S. Pat. No. 7,064,129, Jun. 20, 2006; U.S. patent Ser. No. 10/828,171; U.S. patent Ser. No. 10/828,352; U.S. patent Ser. No. 10/828,466; U.S. patent Ser. No. 10/828,278, as well as U.S. Patent Provisional Serial applications No. 60/812/091; 60/812,077; No. 60/812/078; 61/031,466; and the following Published US patent applications:

1. US Patent Application Publication # US2004/0229884A1, Nov. 18, 2004
2. US Patent Application Publication # US2004/0204425A1, Oct. 14, 2004
3. US Patent Application Publication # US2004/0204424A1, Oct. 14, 2004
4. US Patent Application Publication # US2004/0198749A1, Oct. 7, 2004
5. US Patent Application Publication # US2004/0198748A1, Oct. 7, 2004
6. US Patent Application Publication # US2004/0198747A1, Oct. 7, 2004
7. US Patent Application Publication # US2004/0198746A1, Oct. 7, 2004
8. US Patent Application Publication # US2004/0198745A1, Oct. 7, 2004
9. US Patent Application Publication # US2004/0198744A1, Oct. 7, 2004
10. US Patent Application Publication # US2004/0162296A1, Aug. 19, 2004
11. US Patent Application Publication # US2003/0199456A1, Oct. 23, 2003
12. US Patent Application Publication # US2003/0195160A1, Oct. 16, 2003
13. US Patent Application Publication # US2005/059676A1, Mar. 17, 2005.
14. US Patent Application Publication # US2005/0080091 A1, Apr. 14, 2005.
15. US Patent Application Publication # US2005/00800921 A1, Apr. 14, 2005.
16. US Patent Application Publication # US2005/0090505A1, Apr. 28, 2005.
17. US Patent Application Publication # US2005/0113390A1, May 26, 2005.
18. US Patent Application Publication # US2005/0113389A1, May 26, 2005.
19. US Patent Application Publication # US2005/0113388A1, May 26, 2005.
20. US Patent Application Publication # US2005/0080093A1, Apr. 14, 2005.
21. US Patent Application Publication # US2005/0228182A1, Oct. 13, 2005
22. US Patent Application Publication # US2005/0234072A1, Oct. 20, 2005
23. US Patent Application Publication # US2006/0040954A1, Feb. 23, 2006.
24. US Patent Application Publication # US2006/0052394A1, Mar. 9, 2006.
25. US Patent Application Publication # US2006/0052395A1, Mar. 9, 2006.
26. US Patent Application Publication # US2006/0063780 A1, Mar. 23, 2006.
27. US Patent Application Publication # US2006/0142306 A1, Jun. 29, 2006.
28. US Patent Application Publication # US2006/0142581 A1, Jun. 29, 2006.
29. US Patent Application Publication # US2006/0205738 A1, Sep. 9, 2006.
30. US Patent Application Publication # US2007/0021439 A1, Jan. 25, 2007.
31. US Patent Application Publication # US2007/0032509 A1, Feb. 8, 2007.

Each of the applications and patents cited above is incorporated herein by reference.

The compounds of Formula I discussed above may be a pharmaceutically acceptable salt thereof, and wherein the above compounds are inclusive of all racemates, enantiomers, diastereomers, tautomers, polymorphs and pseudopolymorphs thereof.

The patents and applications cited above are incorporated herein by reference in their entirety, inclusive of specific compounds described therein.

The present invention also provides food and beverage compositions which contain a compound described above.

DETAILED DESCRIPTION OF THE INVENTION

The present invention is based on the discovery that the compounds of formula (I) modulate taste, especially the salty and sour taste responses. The present invention is based on the discovery that certain compounds of formula (I) modulate taste, especially the salty and sour taste responses and are not absorbed systemically. The present invention is also based on the discovery that certain compounds embraced by formula (I) are converted in vivo into metabolic derivatives thereof that have reduced efficacy in blocking both ASIC and sodium channels systemically as compared to the parent administered compound, after they are absorbed from topical (primarily mucosal) surfaces after administration. This important property means that the compounds will have a lower tendency to cause undesired side-effects by blocking sodium channels and ASIC's located in other regions of the body of the recipient, e.g., in the kidneys. The invention concerns further the use of a compound of Formula I as defined herein as an additive to a food composition to enhance the sweetness, salty taste or umami taste of a compound that is present therein and that has such functionality. For example, it is possible to use a compound of Formula I as defined herein to attenuate the salty taste of a food composition. However, it is also possible to use the same compound to modulate the umami taste of a food composition.

The invention also provides the addition of a compound of Formula I as defined herein to a food composition to reduce the saltiness or sourness of a compound therein that has such functionality. While this can be added to any food or beverage, preferred foods for addition of this compound include chocolate, ice-cream, a beverage, a sugar confectionery, a culinary product, or a pet food.

For either situation, the amount desired for administration may be between 0.0001 and 30 mg/kg of the entire food composition.

The invention also relates to a food composition comprising a food and a compound of Formula I as defined herein according to the invention in a taste effective amount sufficient attenuate saltiness or sourness taste characteristics of the food. Preferred foods for addition of this compound include chocolate, ice-cream, a beverage, a sugar confectionery, a culinary product, or a pet food.

The compounds of formula I may be represented as:

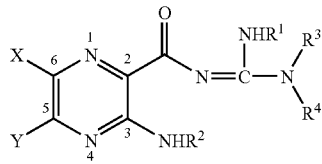

(I)

and racemates, enantiomers, diastereomers, tautomers, polymorphs, pseudopolymorphs and pharmaceutically acceptable salts, thereof, wherein:

X is hydrogen, halogen, trifluoromethyl, lower alkyl, unsubstituted or substituted phenyl, lower alkyl-thio, phenyl-lower alkyl-thio, lower alkyl-sulfonyl, or phenyl-lower alkyl-sulfonyl;

Y is hydrogen, hydroxyl, mercapto, lower alkoxy, lower alkyl-thio, halogen, lower alkyl, unsubstituted or substituted mononuclear aryl, or —N($R^2$)$_2$;

$R^1$ is hydrogen or lower alkyl;

each $R^2$ is, independently, —$R^7$, —(CH$_2$)$_m$—OR$^8$, —(CH$_2$)$_m$—NR$^7$R$^{10}$, —(CH$_2$)$_n$(CHOR$^8$)(CHOR$^8$)$_n$—CH$_2$OR$^8$, —(CH$_2$CH$_2$O)$_m$—R$^8$, —(CH$_2$CH$_2$O)$_m$—CH$_2$CH$_2$NR$^7$R$^{10}$, —(CH$_2$)$_n$—C(=O)NR$^7$R$^{10}$, —(CH$_2$)$_n$—(Z)$_g$—R$^7$, —(CH$_2$)$_m$—NR$^{10}$—CH$_2$(CHOR$^8$)(CHOR$^8$)$_n$—CH$_2$OR$^8$, —(CH—)$_n$—CO—R$^7$, or

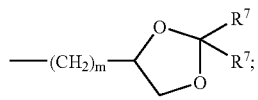

$R^3$ and $R^4$ are each, independently, hydrogen, lower alkyl, hydroxyl-lower alkyl, phenyl, (phenyl)-lower alkyl, (halophenyl)-lower alkyl, ((lower-alkyl)phenyl)-lower-alkyl, ((lower-alkoxy)phenyl)-lower-alkyl, (naphthyl)-lower-alkyl, or (pyridyl)-lower-alkyl, or a group represented by formula A or formula B, with the proviso that at least one of $R^3$ and $R^4$ is a group represented by the formula A or formula B;

    formula A

    formula B $A^1$ is a $C_6$-$C_{15}$-membered aromatic carbocycle substituted with at least one $R^5$ and the remaining substituents are $R^6$;

$A^2$ is a six to fifteen-membered aromatic heterocycle substituted with at least one $R^5$ and the remaining substituents are $R^6$ wherein said aromatic heterocycle comprises 1-4 heteroatoms selected from the group consisting of O, N, and S;

each $R^L$ is, independently, —$R^7$, —(CH$_2$)$_n$—OR$^8$, —O—(CH$_2$)$_m$—OR$^8$, —(CH$_2$)$_n$—NR$^7$R$^{10}$, —O—(CH$_2$)$_m$—NR$^7$R$^{10}$, —(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$, —(CH$_2$)$_n$—C(=O)NR$^7$R$^{10}$, —O—(CH$_2$)$_m$—C(=O)NR$^7$R$^{10}$, —(CH$_2$)$_n$—(Z)$_g$—R$^7$, —O—(CH$_2$)$_m$—(Z)$_g$—R$^7$, —(CH$_2$)$_n$—NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$, —OSO$_3$H, —O-glucuronide, —O-glucose,

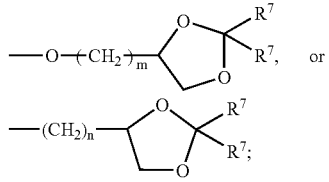

each o is, independently, an integer from 0 to 10;
each p is, independently, an integer from 0 to 10;
with the proviso that the sum of o and p in each contiguous chain is from 1 to 10;
each x is, independently, O, NR$^{10}$, C(=O), CHOH, C(=N—R$^{10}$), CHNR$^7$R$^{10}$, or a single bond;
each $R^5$ is, independently, OH, —(CH$_2$)$_m$—OR$^8$, —O—(CH$_2$)$_m$—OR$^8$, —(CH$_2$)$_n$—NR$^7$R$^{10}$, —O—(CH$_2$)$_m$—NR$^7$R$^{10}$, —(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$, —(CH$_2$)$_n$—C(=O)NR$^7$R$^{10}$, —O—(CH$_2$)$_m$—C(=O)NR$^7$R$^{10}$, —(CH$_2$)$_n$—(Z)$_g$—R$^7$, —O—(CH$_2$)$_m$—(Z)$_g$—R$^7$, —(CH$_2$)$_n$—NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$, —OSO$_3$H, —O-glucuronide, —O-glucose,

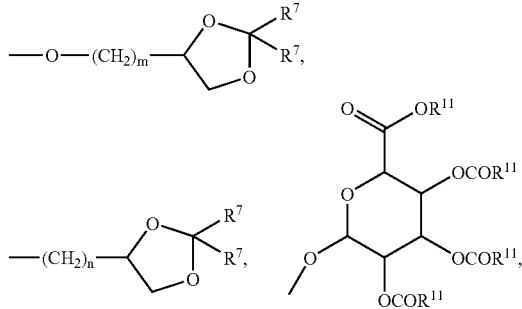

—(CH$_2$)$_n$—CO$_2$R$^{13}$, -Het-(CH$_2$)$_m$—CO$_2$R$^{13}$, —(CH$_2$)$_n$—(Z)$_g$—CO$_2$R$^{13}$, -Het-(CH$_2$)$_m$—(Z)$_g$—CO$_2$R$^{13}$, —(CH$_2$)$_n$—NR$^{10}$—(CH$_2$)$_m$(CHOR$^8$)$_n$—CO$_2$R$^{13}$, -Het-(CH$_2$)$_m$—NR$^{10}$—(CH$_2$)$_m$(CHOR$^8$)$_n$—CO$_2$R$^{13}$, —(CH$_2$)$_n$—(CHOR$^8$)$_m$—CO$_2$R$^{13}$, -Het-(CH$_2$)$_m$—(CHOR$^8$)$_m$—CO$_2$R$^{13}$, —(CH$_2$)$_n$—(CHOR$^8$)$_n$(Z)$_g$—CO$_2$R$^{13}$, -Het-(CH$_2$)$_n$—(CHOR$^8$)$_m$—(Z)$_g$—CO$_2$R$^{13}$, —(CH$_2$)$_n$—(Z)$_g$—(CH$_2$)$_m$—CO$_2$R$^{13}$, —(CH$_2$)$_n$—(Z)$_g$—(CH$_2$)$_m$—CO$_2$R$^{13}$, —(CH$_2$)$_n$—(Z)$_g$(CHOR$^8$)$_m$—(Z)$_g$—CO$_2$R$^{13}$, -Het-(CH$_2$)$_n$—(Z)$_g$—(CHOR$^8$)$_m$—(Z)$_g$—CO$_2$R$^{13}$, —(CH$_2$)$_n$—CONH—C(=NR$^{13}$)—NR$^{13}$R$^{13}$, -Het-(CH$_2$)$_n$—CO—NH—C(=NR$^{13}$)—NR$^{13}$R$^{13}$, —(CH$_2$)$_n$—(Z)$_g$—CONH—C $(=NR^{13})-NR^{13}R^{13}$, -Het-$(CH_2)_n-(Z)_g-CONH-C(=NR^{13})-NR^{13}R^{13}$, $-(CH_2)_n-NR^{10}-(CH_2)_m(CHOR^8)_n-CONH-C(=NR^{13})-NR^{13}R^{13}$, -Het-$(CH_2)_n-NR^{10}-(CH_2)_m(CHOR^8)_n-CONH-C(=NR^{13})-NR^{13}R^{13}$, $-(CH_2)_n-(CHOR^8)_m-CONH-C(=NR^{13})-NR^{13}R^{13}$, -Het-$(CH_2)_n-(CHOR^8)_m-CONH-C(=NR^{13})-NR^{13}R^{13}$, $-(CH_2)_n-(CHOR^8)_m-(Z)_g-CONH-C(=NR^{13})-NR^{13}R^{13}$, -Het-$(CH_2)_n-(CHOR^8)_m-(Z)_g-CONH-C(=NR^{13})-NR^{13}R^{13}$, $-(CH_2)_n-(Z)_g-(CH_2)_mCONH-C(=NR^{13})-NR^{13}R^{13}$, -Het-$(CH_2)_n-(Z)_g-(CH_2)_mCONH-C(=NR^{13})-NR^{13}R^{13}$, $-(CH_2)_n-(Z)_g-(CHOR^8)_m-(Z)_g-CONH-C(=NR^{13})-NR^{13}R^{13}$, -Het-$(CH_2)_n-(Z)_g-(CHOR^8)_m-(Z)_g-CONH-C(=NR^{13})-NR^{13}R^{13}$, $-(CH_2)_n-CONR^7-CONR^{13}R^{13}$, -Het-$(CH_2)_n-CONR^7-CONR^{13}R^{13}$, $-(CH_2)_n-(Z)_g-CONR^7-CONR^{13}R^{13}$, $-(CH_2)_n-(Z)_g-CONR^7-CONR^{13}R^{13}$, $-(CH_2)_n-NR^{10}-(CH_2)_m(CHOR^8)_n-CONR^7-CONR^{13}R^{13}$, -Het-$(CH_2)_n-NR^{10}-(CH_2)_m(CHOR^8)_n-CONR^7-CONR^{13}R^{13}$, $-(CH_2)_n-(CHOR^8)_m-CONR^7-CONR^{13}R^{13}$, -Het-$(CH_2)_n-(CHOR^8)_m-CONR^7-CONR^{13}R^{13}$, $-(CH_2)_n-(CHOR^8)_m-(Z)_g-CONR^7-CONR^{13}R^{13}$, -Het-$(CH_2)_n-(CHOR^8)_m-(Z)_g-CONR^7-CONR^{13}R^{13}$, $-(CH_2)_n-(Z)_g-(CH_2)_mCONR^7-CONR^{13}R^{13}$, -Het-$(CH_2)_n-(Z)_g-(CH_2)_mCONR^7-CONR^{13}R^{13}$, $-(CH_2)_n-(Z)_g(CHOR^8)_m-(Z)_g-CONR^7-CONR^{13}R^{13}$, -Het-$(CH_2)_n-(Z)_g(CHOR^8)_m-(Z)_g-CONR^7-CONR^{13}R^{13}$, $-(CH_2)_n-CONR^7SO_2NR^{13}R^{13}$, -Het-$(CH_2)_m-CONR^7SO_2NR^{13}R^{13}$, $-(CH_2)_n-(Z)_g-CONR^7SO_2NR^{13}R^{13}$, -Het-$(CH_2)_m-(Z)_g-CONR^7SO_2NR^{13}R^{13}$, $-(CH_2)_n-NR^{10}-(CH_2)_m(CHOR^8)_n-CONR^7SO_2NR^{13}R^{13}$, -Het-$(CH_2)_m-NR^{10}-(CH_2)_m(CHOR^8)_n-CONR^7SO_2NR^{13}R^{13}$, $-(CH_2)_n-(CHOR^8)_m-CONR^7SO_2NR^{13}R^{13}$, -Het-$(CH_2)_m-(CHOR^8)_mCONR^7SO_2NR^{13}R^{13}$, $-(CH_2)_n-(Z)_g-(CHOR^8)_m-(Z)_g-CONR^7SO_2NR^{13}R^{13}$, -Het-$(CH_2)_n-(CHOR^8)_m-(Z)_g-CONR^7SO_2NR^{13}R^{13}$, $-(CH_2)_n-(Z)_g-(CH_2)_mCONR^7SO_2NR^{13}R^{13}$, -Het-$(CH_2)_n-(Z)_g-(CH_2)_mCONR^7SO_2NR^{13}R^{13}$, $-(CH_2)_n-(Z)_g-(CHOR^8)_m-(Z)_g-CONR^7SO_2NR^{13}R^{13}$, -Het-$(CH_2)_n-(Z)_g-(CHOR^8)_m-(Z)_g-CONR^7SO_2NR^{13}R^{13}$, $-(CH_2)_n-SO_2NR^{13}R^{13}$, -Het-$(CH_2)_m-SO_2NR^{13}R^{13}$, $-(CH_2)_n-(Z)_g-SO_2NR^{13}R^{13}$, -Het-$(CH_2)_m-(Z)_g-SO_2NR^{13}R^{13}$, $-(CH_2)_n-NR^{10}-(CH_2)_m(CHOR^8)_n-SO_2NR^{13}R^{13}$, -Het-$(CH_2)_m-NR^{10}-(CH_2)_m(CHOR^8)_n-SO_2NR^{13}R^{13}$, $-(CH_2)_n-(CHOR^8)_m-SO_2NR^{13}R^{13}$, -Het-$(CH_2)_m-(CHOR^8)_m-SO_2NR^{13}R^{13}$, $-(CH_2)_n-(CHOR^8)_m-(Z)_g-SO_2NR^{13}R^{13}$, -Het-$(CH_2)_n-(CHOR^8)_m-(Z)_g-SO_2NR^{13}R^{13}$, $-(CH_2)_n-(Z)_g-(CH_2)_mSO_2NR^{13}R^{13}$, -Het-$(CH_2)_n-(Z)_g-(CHOR^8)_m-(Z)_g-SO_2NR^{13}R^{13}$, -Het-$(CH_2)_n-(Z)_g-(CHOR^8)_m-(Z)_g-SO_2NR^{13}R^{13}$, $-(CH_2)_n-CONR^{13}R^{13}$, -Het-$(CH_2)_m-CONR^{13}R^{13}$, $-(CH_2)_n-(Z)_g-CONR^{13}R^{13}$, -Het-$(CH_2)_m-(Z)_g-CONR^{13}R^{13})_3$, $-(CH_2)_n-NR^{10}-(CH_2)_m(CHOR^8)_n-CONR^{13}R^{13}$, -Het-$(CH_2)_m-NR^{10}-(CH_2)_m(CHOR^8)_n-CONR^{13}R^{13}$, $-(CH_2)_n-(CHOR^8)_mCONR^{13}R^{13}$, -Het-$(CH_2)_m-(CHOR^8)_m-CONR^{13}R^{13}$, $-(CH_2)_n-(CHOR^8)_m-(Z)_g-CONR^{13}R^{13}$, -Het-$(CH_2)_n-(CHOR^8)_m-(Z)_g-CONR^{13}R^{13}$, $-(CH_2)_n-(Z)_g-(CH_2)_mCONR^{13}R^{13}$, -Het-$(CH_2)_n-(Z)_g-(CH_2)_mCONR^{13}R^{13}$, $-(CH_2)_n-(Z)_g-(CHOR^8)_m-(Z)_g-CONR^{13}R^{13}$, -Het-$(CH_2)_n-(Z)_g-(CHOR^8)_m-(Z)_g-CONR^{13}R^{13}$, $-(CH_2)_n-CONR^7COR^{13}$, -Het-$(CH_2)_m-(Z)_g-CONR^7COR^{13}$, $-(CH_2)_n-(Z)_g-CONR^7COR^{13}$, -Het-$(CH_2)_m-(Z)_g-CONR^7COR^{13}$, $-(CH_2)_n-NR^{10}-(CH_2)_m(CHOR^8)_n-CONR^7COR^{13}$, -Het-$(CH_2)_m-NR^{10}-(CH_2)_m(CHOR^8)_n-CONR^7COR^{13}$, -Het-$(CH_2)_m-(CHOR^8)_m-CONR^7COR^{13}$, $-(CH_2)_n-(CHOR^8)_m-(Z)_g-CONR^7COR^{13}$, -Het-$(CH_2)_n-(CHOR^8)_m-(Z)_g-CONR^7COR^{13}$, $-(CH_2)_n-(Z)_g-(CH_2)_mCONR^7COR^{13}$, -Het-$(CH_2)_n-(Z)_g-(CH_2)_mCONR^7COR^{13}$, $-(CH_2)_n-(Z)_g-(CHOR^8)_m-(Z)_g-CONR^7COR^{13}$, -Het-$(CH_2)_n-(Z)_g-(CHOR^8)_m-(Z)_g-CONR^7COR^{13}$, $-(CH_2)_n-CONR^7CO_2R^{13}$, -Het-$(CH_2)_m-(Z)_g-CONR^7CO_2R^{13}$, $-(CH_2)_n-NR^{10}-(CH_2)_m(CHOR^8)_n-CONR^7CO_2R^{13}$, -Het-$(CH_2)_m-NR^{10}-(CH_2)_m(CHOR^8)_n-CONR^7CO_2R^{13}$, $-(CH_2)_n-(CHOR^8)_m-CONR^7CO_2R^{13}$, -Het-$(CH_2)_m-(CHOR^8)_m-CONR^7CO_2R^{13}$, $-(CH_2)_n-(CHOR^8)_m-(Z)_g-CONR^7CO_2R^{13}$, -Het-$(CH_2)_n-(CHOR^8)_m-(Z)_g-CONR^7CO_2R^{13}$, $-(CH_2)_n-(Z)_g-(CH_2)_mCONR^7CO_2R^{13}$, -Het-$(CH_2)_n-(Z)_g-(CH_2)_mCONR^7CO_2R^{13}$, $-(CH_2)_n-(Z)_g-(CHOR^8)_m-(Z)_g-CONR^7CO_2R^{13}$, -Het-$(CH_2)_n-(Z)_g-(CHOR^8)_m-(Z)_g-CONR^7CO_2R^{13}$, $-(CH_2)_n-NH-C(=NR^{13})-NR^{13}R^{13}$, -Het-$(CH_2)_m-NH-C(=NR^{13})-NR^{13}R^{13}$, $-(CH_2)_n-(Z)_g-NH-C(=NR^{13})-NR^{13}R^{13}$, -Het-$(CH_2)_m-(Z)_g-NH-C(=NR^{13})-NR^{13}R^{13}$, $-(CH_2)_n-NR^{10}-(CH_2)_m(CHOR^8)_n-NH-C(=NR^{13})-NR^{13}R^{13}$, -Het-$(CH_2)_m-NR^{10}-(CH_2)_m(CHOR^8)_n-NH-C(=NR^{13})-NR^{13}R^{13}$, $-(CH_2)_n-(CHOR^8)_m-NH-C(=NR^{13})-NR^{13}R^{13}$, -Het-$(CH_2)_n-(CHOR^8)_m-NH-C(=NR^{13})-NR^{13}R^{13}$, $-(CH_2)_n-(CHOR^8)_m-(Z)_g-NH-C(=NR^{13})-NR^{13}R^{13}$, -Het-$(CH_2)_n-(CHOR^8)_m-(Z)_g-NH-C(=NR^{13})-NR^{13}R^{13}$, $-(CH_2)_n-(Z)_g-(CH_2)_mNH-C(=NR^{13})-NR^{13}R^{13}$, -Het-$(CH_2)_n-(Z)_g-(CH_2)_mNH-C(=NR^{13})-NR^{13}R^{13}$, $-(CH_2)_n-(Z)_g-(CHOR^8)_m-(Z)_g-NH-C(=NR^{13})-NR^{13}R^{13}$, -Het-$(CH_2)_n-(Z)_g-(CHOR^8)_m-(Z)_g-NH-C(=NR^{13})-NR^{13}R^{13}$, $-(CH_2)_n-C(=NR^{13})-NR^{13}R^{13}$, Het-$(CH_2)_m-C(=NH)-NR^{13}R^{13}$, $-(CH_2)_n-(Z)_g-C(=NH)-NR^{13}R^{13}$, Het-$(CH_2)_m-(Z)_g-C(=NH)-NR^{13}R^{13}$, $-(CH_2)_n-NR^{10}-(CH_2)_m(CHOR^8)_n-C(=NR^{13})-NR^{13}R^{13}$, Het-$(CH_2)_m-NR^{10}-(CH_2)_m(CHOR^8)_n-C(=NR^{13})-NR^{13}R^{13}$, $-(CH_2)_n-(CHOR^8)_m-C(=NR^{13})-NR^{13}R^{13}$, -Het-$(CH_2)_m-(CHOR^8)_m-C(=NR^{13})-NR^{13}R^{13}$, $-(CH_2)_n-(CHOR^8)_m-(Z)_g-C(=NR^{13})-NR^{13}R^{13}$, -Het-$(CH_2)_n-(CHOR^8)_m-(Z)_g-C(=NR^{13})-NR^{13}R^{13}$, $-(CH_2)_n-(Z)_g-(CH_2)_m-C(=NHC(=NR^{13})-NR^{13}R^{13}$, Het-$(CH_2)_n-(Z)_g-(CH_2)_m-C(=NR^{13})-NR^{13}R^{13}$, $-(CH_2)_n-(Z)_g-(CHOR^8)_m-(Z)_g-C(=NR^{13})-NR^{13}R^{13}$, -Het-$(CH_2)_n-(Z)_g-(CHOR^8)_m-(Z)_g-C(=NR^{13})-NR^{13}R^{13}$, $-(CH_2)_n-NR^{12}R^{12}$, $-O-(CH_2)_m-NR^{12}R^{12}$, $-O-(CH_2)_n-NR^{12}R^{12}$, $-O-(CH_2)_m(Z)_gR^{12}$, $-(CH_2)_nNR^{11}R^{11}$, $-O-(CH_2)_mNR^{11}R^{11}$, $-(CH_2)_n-N^\oplus(R^{11})_3$, $-O-(CH_2)_m-N^\oplus(R^{11})_3$, $-(CH_2)_n-(Z)_g-(CH_2)_m-NR^{10}R^{10}$, $-O-(CH_2)_n-(Z)_g-(CH_2)_m-NR^{10}R^{10}$, $-(CH_2CH_2O)_m-CH_2CH_2NR^{12}R^{12}$, $-O-(CH_2CH_2O)_m-CH_2CH_2NR^{12}R^{12}$, $-(CH_2)_n-(C=O)NR^{12}R^{12}$, $-O-(CH_2)_m-(C=O)NR^{12}R^{12}$, $-O-(CH_2)_m-(CHOR^8)_mCH_2NR^{10}-(Z)_g-R^{10}$, $-(CH_2)_n-(CHOR^8)_mCH_2-NR^{10}-(Z)_g-R^{10}$, $-(CH_2)_nNR^{10}-O(CH_2)_m(CHOR^8)_nCH_2NR^{10}-(Z)_g-R^{10}$, $-O(CH_2)_m-NR^{10}-(CH_2)_m-(CHOR^8)_nCH_2NR^{10}-(Z)_g-R^{10}$, -(Het)-$(CH_2)_m-OR^8$, -(Het)-$(CH_2)_m-NR^7R^{10}$, -(Het)-$(CH_2)_m(CHOR^8)(CHOR^8)_n-CH_2OR^8$, -(Het)-$(CH_2CH_2O)_m-R^8$, -(Het)-$(CH_2CH_2O)_m-CH_2CH_2NR^7R^{10}$, -(Het)-$(CH_2)_m-C(=O)NR^7R^{10}$, -(Het)-$(CH_2)_m-(Z)_g-R^7$, -(Het)-$(CH_2)_n-NR^{10}-CH_2(CHOR^8)(CHOR^8)_m-CH_2OR^8$, -(Het)-$(CH_2)_m-CO_2R^7$, -(Het)-$(CH_2)_m-NR^{12}R^{12}$, -(Het)-$(CH_2)_n-NR^{12}R^{12}$, -(Het)-$(CH_2)_m-(Z)_gR^{12}$, -(Het)-

$(CH_2)_m NR^{11}R^{11}$, -(Het)-$(CH_2)_m$—$N^{\oplus}$-$(R^{11})_3$, -(Het)-$(CH_2)_m$—$(Z)_g$—$(CH_2)_m$—$NR^{10}R^{10}$, -(Het)-$(CH_2CH_2O)_m$—$CH_2CH_2NR^{12}R^{12}$, -(Het)-$(CH_2)_m$—$C(=O)NR^{12}R^{12}$, -(Het)-$(CH_2)_m$—$(CHOR^8)_m CH_2 NR^{10}$—$(Z)_g$—$R^{10}$, -(Het)-$(CH_2)_m$—$NR^{10}$—$(CH_2)_m$—$(CHOR^8)_n CH_2 NR^{10}$—$(Z)_g$—$R^{10}$, —$(CH_2)_n(CHOR^8)(CHOR^8)_n$—$CH_2OR^8$, —O—$(CH_2)_m(CHOR^8)(CHOR^8)_n$—$CH_2OR^8$, —$(CH_2)_n$—$NR^{10}$—$CH_2(CHOR^8)(CHOR^8)_n$—$CH_2OR^8$, —O—$(CH_2)_m$—$NR^{10}$—$CH_2(CHOR^8)(CHOR^8)_n$—$CH_2OR^8$, Link-$(CH_2)_n$—CAP, Link-$(CH_2)_n(CHOR^8)(CHOR^8)_n$—CAP, Link-$(CH_2CH_2O)_m$—$CH_2$—CAP, Link-$(CH_2CH_2O)_m$—$CH_2CH_2$—CAP, Link-$(CH_2)_n$—$(Z)_g$-CAP, Link-$(CH_2)_n(Z)_g$—$(CH_2)_m$—CAP, Link-$(CH_2)_n$—$NR^{13}$—$CH_2(CHOR^8)(CHOR^8)_n$—CAP, Link-$(CH_2)_n$—$(CHOR^8)_m CH_2$—$NR^{13}$—$(Z)_g$-CAP, Link-$(CH_2)_n NR^{13}$—$(CH_2)_m(CHOR^8)_n CH_2 NR^{13}$—$(Z)_g$-CAP, -Link-$(CH_2)_m$—$(Z)_g$—$(CH_2)_m$—CAP, Link-NH—$C(=O)$—NH—$(CH_2)_m$—CAP, Link $(CH_2)_m$—$C(=O)NR^{13}$—$(CH_2)_m$—$C(=O)NR^{10}R^{10}$, Link $(CH_2)_m$—$C(=O)NR^{13}$—$(CH_2)_m$—CAP, Link $(CH_2)_m$—$C(=O)NR^{11}R^{11}$, Link-$(CH_2)_m$—$C(=O)NR^{12}R^{12}$, Link-$(CH_2)_n$—$(Z)_g$—$(CH_2)_m$—$(Z)_g$-CAP, Link—$(Z)_g$—$(CH_2)_m$-Het-$(CH_2)_m$—CAP, Link-$(CH_2)_n$—$CR^{11}R^{11}$-CAP, Link-$(CH_2)_n(CHOR^8)(CHOR^8)_n$—$CR^{11}R^{11}$-CAP, Link-$(CH_2CH_2O)_m$—$CH_2$—$CR^{11}R^{11}$-CAP, Link-$(CH_2CH_2O)_m$—$CH_2CH_2$—$CR^{11}R^{11}$-CAP, Link-$(CH_2)_n$—$(Z)_g$—$CR^{11}R^{11}$-CAP, Link-$(CH_2)_n(Z)_g$—$(CH_2)_m$—$CR^{11}R^{11}$-CAP, Link-$(CH_2)_n$—$NR^{13}$—$CH_2(CHOR^8)(CHOR^8)_n$—$CR^{11}R^{11}$-CAP, Link-$(CH_2)_n$—$(CHOR^8)_m CH_2$—$NR^{13}$—$(Z)_g$—$CR^{11}R^{11}$-CAP, Link-$(CH_2)_n NR^{13}$—$(CH_2)_m(CHOR^8)_n CH_2 NR^{13}$—$(Z)_g$—$CR^{11}R^{11}$-CAP, Link-$(CH_2)_m$—$(Z)_g$—$(CH_2)_m$—$CR^{11}R^{11}$-CAP, Link NH—$C(=O)$—NH—$(CH_2)_m$—$CR^{11}R^{11}$-CAP, Link-$(CH_2)_m$—$C(=O)NR^{13}$—$(CH_2)_m$—$CR^{11}R^{11}$-CAP, Link-$(CH_2)_n$—$(Z)_g$—$(CH_2)_m$—$(Z)_g$—$CR^{11}R^{11}$-CAP, or Link—$(Z)_g$—$(CH_2)_m$-Het-$(CH_2)_m$—$CR^{11}R^{11}$-CAP;

each $R^6$ is, independently, $R^5$, —$R^7$, —$OR^{11}$, —$N(R^7)_2$, —$(CH_2)_m$—$OR^8$, —O—$(CH_2)_m$—$OR^8$, —$(CH_2)_n$—$NR^7R^{10}$, —O—$(CH_2)_m$—$NR^7R^{10}$, —$(CH_2)_n(CHOR^8)(CHOR^8)_n$—$CH_2OR^8$, —O—$(CH_2)_m(CHOR^8)(CHOR^8)_n$—$CH_2OR^8$, —$(CH_2CH_2O)_m$—$R^8$, —O—$(CH_2CH_2O)_m$—$R^8$, —$(CH_2CH_2O)_m$—$CH_2CH_2NR^7R^{10}$, —O—$(CH_2CH_2O)_m$—$CH_2CH_2NR^7R^{10}$, —$(CH_2)_n$—$C(=O)NR^7R^{10}$, —O—$(CH_2)_m$—$C(=O)NR^7R^{10}$, —$(CH_2)_n$—$(Z)_g$—$R^7$, —O—$(CH_2)_m$—$(Z)_g$—$R^7$, —$(CH_2)_n$—$NR^{10}$—$CH_2(CHOR^8)(CHOR^8)_n$—$CH_2OR^8$, —O—$(CH_2)_m$—$NR^{10}$—$CH_2(CHOR^8)(CHOR^8)_n$—$CH_2OR^8$, —$(CH_2)_n$—$CO_2R^7$, —O—$(CH_2)_m$—$CO_2R^7$, —$OSO_3H$, —O-glucuronide, —O-glucose,

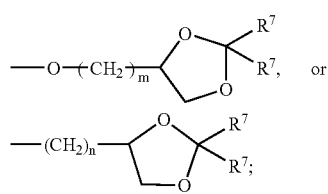

wherein when two $R^6$ are —$OR^{11}$ and are located adjacent to each other on the aromatic carbocycle or aromatic heterocycle, the two $OR^{11}$ may form a methylenedioxy group;

each $R^7$ is, independently, hydrogen, lower alkyl, phenyl, substituted phenyl or —$CH_2(CHOR^8)_m$—$CH_2OR^8$;

each $R^8$ is, independently, hydrogen, lower alkyl, —$C(=O)$—$R^{11}$, glucuronide, 2-tetrahydropyranyl, or

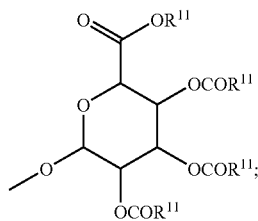

each $R^9$ is, independently, —$CO_2R^7$, —$CON(R^7)_2$, —$SO_2CH_3$, —$C(=O)R^7$, —$CO_2R^{13}$, —$CON(R^{13})_2$, —$SO_2CH_2R^{13}$, or —$C(=O)R^{13}$;

each $R^{10}$ is, independently, —H, —$SO_2CH_3$, —$CO_2R^7$, —$C(=O)NR^7R^9$, —$C(=O)R^7$, or —$CH_2$—$(CHOH)_n$—$CH_2OH$;

each Z is, independently, —(CHOH)—, —$C(=O)$—, —$(CHNR^7R^{10})$—, —$(C=NR^{10})$—, —$NR^{10}$—, —$(CH_2)_n$—, —$(CHNR^{13}R^{13})$—, —$(C=NR^{13})$—, or —$NR^{13}$—;

each $R^{11}$ is, independently, hydrogen, lower alkyl, phenyl lower alkyl or substituted phenyl lower alkyl;

each $R^{12}$ is, independently, —$SO_2CH_3$, —$CO_2R^7$, —$C(=O)NR^7R^9$, —$C(=O)R^7$, —$CH_2(CHOH)_n$—$CH_2OH$, —$CO_2R^{13}$, —$C(=O)NR^{13}R^{13}$, or —$C(=O)R^{13}$;

each $R^{13}$ is, independently, $R^7$, $R^{10}$, —$(CH_2)_m$—$NR^7R^{10}$, —$(CH_2)_m$—$NR^7R^7$, —$(CH_2)_m$—$NR^{11}R^{11}$, —$(CH_2)_m$—$(NR^{11}R^{11}R^{11})^+$, —$(CH_2)_m$—$(CHOR^8)_m$—$(CH_2)_m NR^{11}R^{11}$, —$(CH_2)_m$—$(CHOR^8)_m$—$(CH_2)_m NR^7R^{10}$, —$(CH_2)_m$—$NR^{10}R^{10}$, —$(CH_2)_m$—$(CHOR^8)_m$—$(CH_2)_m$—$(NR^{11}R^{11}R^{11})^+$, —$(CH_2)_m$—$(CHOR^8)_m$—$(CH_2)_m NR^7R^7$,

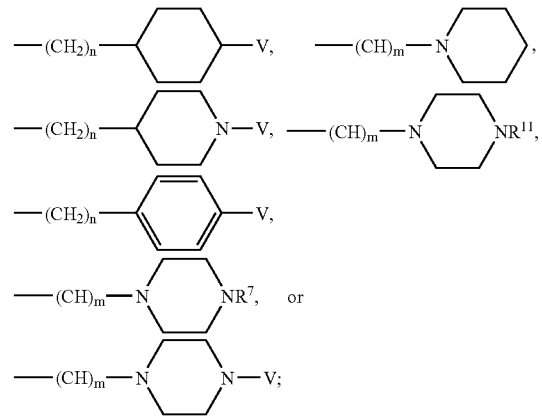

with the proviso that in the moiety —$NR^{13}R^{13}$, the two $R^{13}$ along with the nitrogen to which they are attached may, optionally, form a ring selected from:

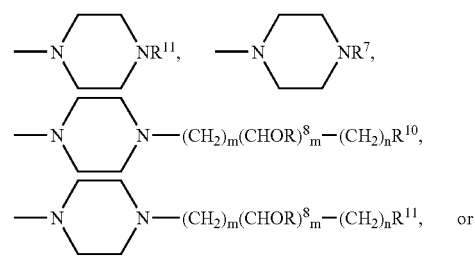

-continued

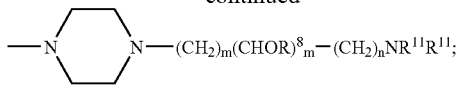

each V is, independently, —$(CH_2)_m$—$NR^7R^{10}$, —$(CH_2)_m$—$NR^7R^7$, —$(CH_2)_m$—$(NR^{11}R^{11}R^{11})^+$, —$(CH_2)_n$—$(CHOR^8)_m$—$(CH_2)_m NR^7R^{10}$, —$(CH_2)_n$—$NR^{10}R^{10}$—$(CH_2)_n$—$(CHOR^8)_m$—$(CH_2)_m NR^7R^7$, —$(CH_2)_n$—$(CHOR^8)_m$—$(CH_2)_m$—$(NR^{11}R^{11}R^{11})^+$ with the proviso that when V is attached directly to a nitrogen atom, then V can also be, independently, $R^7$, $R^{10}$, or $(R^{11})_2$;

each $R^{14}$ is, independently, H, $R^{12}$, —$(CH_2)_n$—$SO_2CH_3$, —$(CH_2)_n$—$CO_2R^{13}$, —$(CH_2)_n$—$C(=O)NR^{13}R^{13}$, —$(CH_2)_n$—$C(=O)R^{13}$, —$(CH_2)_n$—$(CHOH)_n$—$CH_2OH$, —NH—$(CH_2)_n$—$SO_2CH_3$, NH$(CH_2)_n$—$C(=O)R^{11}$, NH—$C(=O)$—NH—$C(=O)R^{11}$, —$C(=O)NR^{13}R^{13}$, —$OR^{11}$, —NH—$(CH_2)_n$—$R^{10}$, —Br, —Cl, —F, —I, $SO_2NHR^{11}$, —$NHR^{13}$, NH—$C(=O)NR^{13}R^{13}$, —$(CH_2)_n$—$NHR^{13}$, or —NH—$(CH_2)_n$—$C(=O)$—$R^{13}$;

each g is, independently, an integer from 1 to 6;

each m is, independently, an integer from 1 to 7;

each n is, independently, an integer from 0 to 7;

each -Het- is, independently, —$N(R^7)$—, —$N(R^{10})$—, —S—, —SO—, —$SO_2$—, —O—, —$SO_2NH$—, —$NHSO_2$—, —$NR^7CO$—, —$CONR^7$—, —$N(R^{13})$—, —$SO_2NR^{13}$—, —$NR^{13}CO$—, or —$CONR^{13}$—;

each Link is, independently, —O—, —$(CH_2)_n$—, —$O(CH_2)_m$—, —$NR^{13}$—$C(=O)$—$NR^{13}$—, —$NR^{13}$—$C(=O)$—$(CH_2)_m$—, —$C(=O)NR^{13}$—$(CH_2)_m$—, —$(CH_2)_n$—$(Z)_g$—$(CH_2)_n$—, —S—, —SO—, —$SO_2$—, —$SO_2NR^7$—, —$SO_2NR^{10}$—, or -Het-;

each CAP is, independently, thiazolidinedione, oxazolidinedione, -heteroaryl—$C(=O)NR^{13}R^{13}$, heteroaryl-W, —CN, —O—$C(=S)NR^{13}R^{13}$, —$(Z)_gR^{13}$, —$CR^{10}((Z)_gR^{13})((Z)_gR^{13})$, —$C(=O)OAr$, —$C(=O)NR^{13}Ar$, imidazoline, tetrazole, tetrazole amide, —$SO_2NHR^{13}$, —$SO_2NH$—$C(R^{13}R^{13})$—$(Z)_g$—$R^{13}$, a cyclic sugar or oligosaccharide, a cyclic amino sugar, oligosaccharide, —$CR^{10}($—$(CH_2)_m$—$R^9)($—$(CH_2)_m$—$R^9)$, —N($—(CH_2)_m$—$R^9)($—$(CH_2)_m$—$R^9)$, —$NR^{13}($—$(CH_2)_m$—$CO_2R^{13})$,

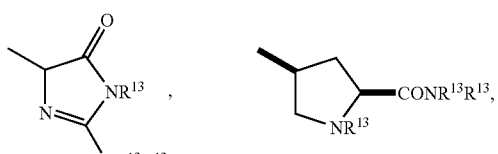

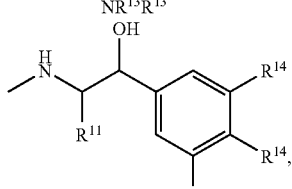

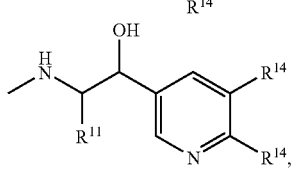

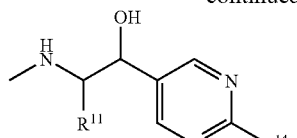

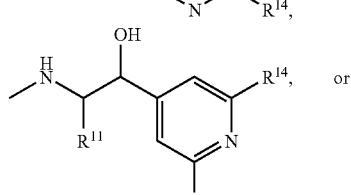

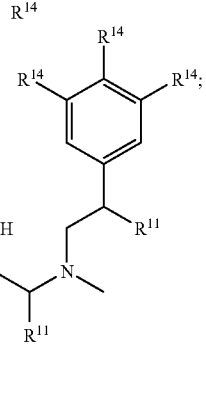

each Ar is, independently, phenyl, substituted phenyl, wherein the substituents of the substituted phenyl are 1-3 substituents independently selected from the group consisting of OH, $OCH_3$, $NR^{13}R^{13}$, Cl, F, and $CH_3$, or heteroaryl; and each W is, independently, thiazolidinedione, oxazolidinedione, heteroaryl—$C(=O)NR^{13}R^{13}$, —CN, —O—$C(=S)NR^{13}R^{13}$, —$(Z)_gR^{13}$, —$CR^{10}((Z)_gR^{13})((Z)_gR^{13})$, —$C(=O)OAr$, —$C(=O)NR^{13}Ar$, imidazoline, tetrazole, tetrazole amide, —$SO_2NHR^{13}$, —$SO_2NH$—$C(R^{13}R^{13})$—$(Z)_g$—$R^{13}$, a cyclic sugar or oligosaccharide, a cyclic amino sugar, oligosaccharide,

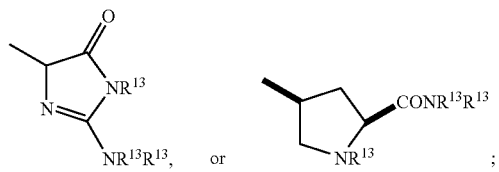

with the proviso that when any —$CHOR^8$— or $CH_2OR^8$ groups are located 1,2- or 1,3- with respect to each other, the $R^8$ groups may, optionally, be taken together to form a cyclic mono- or di-substituted 1,3-dioxane or 1,3-dioxolane.

In the compounds represented by formula (I), X may be hydrogen, halogen, trifluoromethyl, lower alkyl, lower cycloalkyl, unsubstituted or substituted phenyl, lower alkyl-thio, phenyl-lower alkyl-thio, lower alkyl-sulfonyl, or phenyl-lower alkyl-sulfonyl. Halogen is preferred.

Examples of halogen include fluorine, chlorine, bromine, and iodine. Chlorine and bromine are the preferred halogens. Chlorine is particularly preferred. This description is applicable to the term "halogen" as used throughout the present disclosure.

As used herein, the term "lower alkyl" means an alkyl group having less than 8 carbon atoms. This range includes all specific values of carbon atoms and subranges there between, such as 1, 2, 3, 4, 5, 6, and 7 carbon atoms. The term "alkyl" embraces all types of such groups, e.g., linear, branched, and cyclic alkyl groups. This description is applicable to the term "lower alkyl" as used throughout the present disclosure. Examples of suitable lower alkyl groups include methyl, ethyl, propyl, cyclopropyl, butyl, isobutyl, etc.

Substituents for the phenyl group include halogens. Particularly preferred halogen substituents are chlorine and bromine.

Y may be hydrogen, hydroxyl, mercapto, lower alkoxy, lower alkyl-thio, halogen, lower alkyl, lower cycloalkyl, mononuclear aryl, or $-N(R^2)_2$. The alkyl moiety of the lower alkoxy groups is the same as described above. Examples of mononuclear aryl include phenyl groups. The phenyl group may be unsubstituted or substituted as described above. The preferred identity of Y is $-N(R^2)_2$. Particularly preferred are such compounds where each $R^2$ is hydrogen.

$R^1$ may be hydrogen or lower alkyl. Hydrogen is preferred for $R^1$.

Each $R^2$ may be, independently, $-R^7$, $-(CH_2)_m-OR^8$, $-(CH_2)_m-NR^7R^{10}$, $-(CH_2)_n(CHOR^8)(CHOR^8)_n-CH_2OR^8$, $-(CH_2CH_2O)_m-R^8$, $-(CH_2CH_2O)_m-CH_2CH_2NR^7R^{10}$, $-(CH_2)_n-C(=O)NR^7R^{10}$, $-(CH_2)-(Z)_g-R^7$, $-(CH_2)_m-NR^{10}-CH_2(CHOR^8)(CHOR^8)_n-CH_2OR^8$, $-(CH_2)_n-CO_2R^7$, or

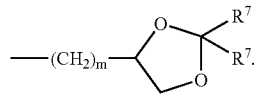

Hydrogen and lower alkyl, particularly $C_1$-$C_3$ alkyl, are preferred for $R^2$. Hydrogen is particularly preferred.

$R^3$ and $R^4$ may be, independently, hydrogen, lower alkyl, hydroxyl-lower alkyl, phenyl, (phenyl)-lower alkyl, (halophenyl)-lower alkyl, ((lower-alkyl)phenyl)-lower-alkyl), (lower-alkoxyphenyl)-lower alkyl, (naphthyl)-lower alkyl, (pyridyl)-lower alkyl or a group represented by $-(C(R^L)_2)_o\text{-x-}(C(R^L)_2)_pA^1$ or $-(C(R^L)_2)_o\text{-x-}(C(R^L)_2)_pA^2$, provided that at least one of $R^3$ and $R^4$ is a group represented by $-(C(R^L)_2)_o\text{-x-}(C(R^L)_2)_pA^1$ or $-(C(R^L)_2)_o\text{-x-}(C(R^L)_2)_pA^2$.

Preferred compounds are those where one of $R^3$ and $R^4$ is hydrogen and the other is represented by $-(C(R^L)_2)_o\text{-x-}(C(R^L)_2)_pA^1$ or $-(C(R^L)_2)_o\text{-x-}(C(R^L)_2)_pA^2$. In a particularly preferred aspect one of $R^3$ and $R^4$ is hydrogen and the other of $R^3$ or $R^4$ is represented by $-(C(R^L)_2)_o\text{-x-}(C(R^L)_2)_pA^1$. In another particularly preferred aspect one of $R^3$ and $R^4$ is hydrogen and the other of $R^3$ or $R^4$ is represented by $-(C(R^L)_2)_o\text{-x-}(C(R^L)_2)_pA^2$.

A moiety $-(C(R^L)_2)_o\text{-x-}(C(R^L)_2)_p-$ defines an alkylene group bonded to the group $A^1$ or $A^2$. The variables o and p may each, independently, be an integer from 0 to 10, subject to the proviso that the sum of o and p in the chain is from 1 to 10. Thus, o and p may each be 0, 1, 2, 3, 4, 5, 6, 7, 8, 9, or 10. Preferably, the sum of o and p is from 2 to 6. In a particularly preferred embodiment, the sum of o and p is 4.

The linking group in the alkylene chain, x, may be, independently, O, $NR^{10}$, $C(=O)$, CHOH, $C(=N-R^{10})$, $CHNR^7R^{10}$, or a single bond;

Therefore, when x is a single bond, the alkylene chain bonded to the ring is represented by the formula $-(C(R^L)_2)_{o+p}-$, in which the sum o+p is from 1 to 10.

Each $R^L$ may be, independently, $-R^7$, $-(CH_2)_n-OR^8$, $-O-(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose,

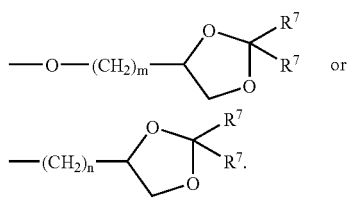

The term $-O$-glucuronide, unless otherwise specified, means a group represented by

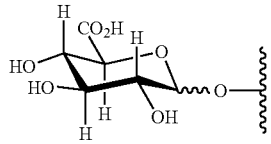

wherein the $\sim\sim\sim$O means the glycosidic linkage can be above or below the plane of the ring.

The term $-O$-glucose, unless otherwise specified, means a group represented by

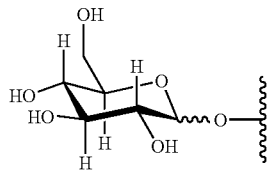

wherein the $\sim\sim\sim$O means the glycosidic linkage can be above or below the plane of the ring.

The preferred $R^L$ groups include $-H$, $-OH$, $-N(R^7)_2$, especially where each $R^7$ is hydrogen.

In the alkylene chain in $-(C(R^L)_2)_o\text{-x-}(C(R^L)_2)_pA^1$ or $(C(R^L)_2)_o\text{-x-}(C(R^L)_2)_pA^2$, it is preferred that when one $R^L$ group bonded to a carbon atoms is other than hydrogen, then the other $R^L$ bonded to that carbon atom is hydrogen, i.e., the formula $-CHR^L-$. It is also preferred that at most two $R^L$ groups in an alkylene chain are other than hydrogen, wherein the other $R^L$ groups in the chain are hydrogens. Even more preferably, only one $R^L$ group in an alkylene chain is other than hydrogen, wherein the other $R^L$ groups in the chain are hydrogens. In these embodiments, it is preferable that x is a single bond.

In another particular embodiment of the invention, all of the $R^L$ groups in the alkylene chain are hydrogen. In these embodiments, the alkylene chain is represented by the formula $-(CH_2)_o\text{-x-}(CH_2)_p-$.

$A^1$ is a $C_6$-$C_{15}$-membered aromatic carbocycle substituted with at least one $R^5$ and the remaining substituents are $R^6$. The term aromatic is well known term of chemical art and designates conjugated systems of 4n'+2 electrons that are within a ring system, that is with 6, 10, 14, etc. π-electrons wherein, according to the rule of Huckel, n' is 1, 2, 3, etc. The 4n'+2 electrons may be in any size ring including those with partial saturation so long as the electrons are conjugated. For instance, but not by way of limitation, 5H-cyclohepta-1,3,5-triene, benzene, naphthalene, 1,2,3,4-tetrahydronaphthalene etc. would all be considered aromatic.

The $C_6$-$C_{15}$ aromatic carbocycle may be monocyclic, bicyclic, or tricyclic and may include partially saturated rings. Non-limiting examples of these aromatic carbocycles comprise benzene, 5H-cyclohepta-1,3,5-triene, naphthalene, phenanthrene, azulene, anthracene, 1,2,3,4-tetrahydronapthalene, 1,2-dihydronapthalene, indene, 5H-dibenzo[a,d]cycloheptene, etc.

The $C_6$-$C_{15}$ aromatic carbocycle may be attached to the —$(C(R^L)_2)_o$-x-$(C(R^L)_2)_p$— moiety through any ring carbon atom as appropriate, unless otherwise specified. Therefore, when partially saturated bicyclic aromatic is 1,2-dihydronapthalene, it may be 1,2-dihydronapthalen-1-yl, 1,2-dihydronapthalen-3-yl, 1,2-dihydronapthalen-5-yl, etc. In a preferred embodiment $A^1$ is phenyl, indenyl, napthalenyl, 1,2-dihydronapthalenyl, 1,2,3,4-tetrahydronapthalenyl, anthracenyl, fluorenyl, phenanthrenyl, azulenyl, cyclohepta-1,3,5-trienyl or 5H-dibenzo[a,d]cycloheptenyl. In another preferred embodiment, $A^1$ is phenyl. In another preferred embodiment, $A^1$ is napthalen-1-yl. In another preferred embodiment, $A^1$ is napthalen-2-yl.

In another preferred embodiment, $A^1$ is

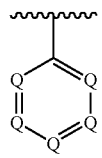

wherein each Q is, independently, C—H, C—$R^5$, or C—$R^6$, with the proviso that at least one Q is C—$R^5$. Therefore, Q may be 1, 2, 3, 4, or 5 C—H. In a particularly preferred embodiment, each $R^6$ is H.

In another preferred embodiment, $A^1$ is

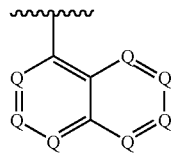

wherein each Q is, independently, C—H, C—$R^5$, or C—$R^6$, with the proviso that at least one Q is C—$R^5$. Therefore, Q may be 1, 2, 3, 4, 5, or 6 C—H. Therefore, Q may be 1, 2, 3, 4, 5, or 6 C—$R^6$. In a particularly preferred embodiment, each $R^6$ is H.

In another preferred embodiment, $A^1$ is

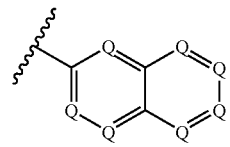

wherein each Q is, independently, C—H, C—$R^5$, C—$R^6$, with the proviso that at least one Q is C—$R^5$. Therefore, Q may be 1, 2, 3, 4, 5, or 6 C—H. Therefore, Q may be 1, 2, 3, 4, 5, or 6 C—$R^6$. In a particularly preferred embodiment, each $R^6$ is H.

In a particularly preferred embodiment, $A^1$ is

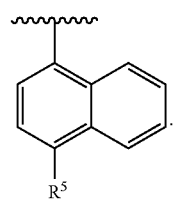

In another particularly preferred embodiment, $A^1$ is

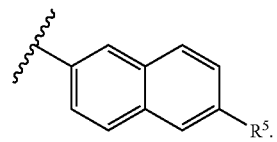

In another particularly preferred embodiment, $A^1$ is

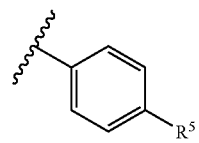

$A^2$ is a six to fifteen-membered aromatic heterocycle substituted with at least one $R^5$ and the remaining substituents are $R^6$ wherein the aromatic heterocycle comprises 1-4 heteroatoms selected from the group consisting of O, N, and S.

The six to fifteen-membered aromatic heterocycle may be monocyclic, bicyclic, or tricyclic and may include partially saturated rings. Non limiting examples of these aromatic heterocycles include pyridyl, 1H-azepine, benzo[b]furan, benzo[b]thiophene, isobenzofuran, isobenzothiophene, 2,3-dihydrobenzo[b]furan, benzo[b]thiophene, 2,3-dihydrobenzo[b]thiophene, indolizine, indole, isoindole benzoxazole, benzimidazole, indazole, benzisoxazole, benzisothizole, benzopyrazole, benzoxadiazole, benzothiadiazole, benzotriazole, purine, quinoline, 1,2,3,4-tetrahydroquinoline, 3,4-dihydro-2H-chromene, 3,4-dihydro-2H-thiochromene, isoquinoline, cinnoline, quinolizine, phthalazine, quinoxaline, quinazoline, naphthiridine, pteridine, benzopyrane, pyrrolopyridine, pyrrolopyrazine, imidazopyrdine, pyrrolopyrazine, thienopyrazine, furopyrazine, isothiazolopyrazine, thiazolopyrazine, isoxazolopyrazine, oxazolopyrazine, pyrazolopyrazine, imidazopyrazine, pyrrolopyrimidine, thienopyrimidine, furopyrimidine, isothiazolopyrimidine, thiazolopyrimidine, isoxazolopyrimidine, oxazolopyrimidine, pyrazolopyrimidine, imidazopyrimidine, pyrrolopyridazine, thienopyridazine, furopyridazine, isothiazolopyridazine, thiazolopyridazine, oxazolopyridazine, thiadiazolopyrazine, oxadiazolopyrimidine, thiadiazolopyrimidine, oxadiazolopyridazine, thiazolopyridazine, imidazooxazole, imidazothiazole, imidazoimidazole, isoxazolotriazine, isothiazolotriazine, oxazolotriazine, thiazolotriazine, carbazole, acridine, phenazine, phenothiazine, phenooxazine, and 5H-dibenz[b,f]azepine, 10,11-dihydro-5H-dibenz[b,f]azepine, etc.

The six to fifteen-membered aromatic heterocycle may be attached to the —$(C(R^L)_2)_o$-x-$(C(R^L)_2)_p$— moiety through any ring carbon atom or ring nitrogen atom so long as a quanternary nitrogen atom is not formed by the attachment. Therefore, when partially saturated aromatic heterocycle is 1H-azepine, it may be 1H-azepin-1-yl, 1H-azepin-2-yl, 1H-azepin-3-yl, etc. Preferred aromatic heterocycles are pyridyl, indolizinyl, indolyl, isoindolyl, indolinyl, benzo[b]furanyl, 2,3-dihydrobenzo[b]furanyl, benzo[b]thiophenyl, 2,3-dihydrobenzo[b]thiophenyl, indazolyl, benzimidazolyl, benzthiazolyl, purinyl, quinolinyl, 1,2,3,4-tetrahydroquinolinyl, 3,4-dihydro-2H-chromenyl, 3,4-dihydro-2H-thiochromenyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, dibenzofuranyl, dibenzothiophenyl, 1H-azepinyl, 5H-dibenz[b,f]azepinyl, are 10,11-dihydro-5H-dibenz[b,f]azepinyl.

In another preferred embodiment, $A^2$ is

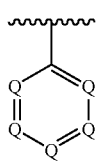

wherein each Q is, independently, C—H, C—$R^5$, C—$R^6$, or a nitrogen atom, with the proviso that at least one Q is nitrogen and one Q is C—$R^5$, and at most three Q in a ring are nitrogen atoms. Therefore, in any one ring, each Q may be 1, 2, or 3 nitrogen atoms. In a preferred embodiment, only one Q in each ring is nitrogen. In another preferred embodiment, only a single Q is nitrogen. Optionally, 1, 2, 3, or 4 Q may be C—$R^6$. Optionally, Q may be 1, 2, 3, or 4 C—H. In a particularly preferred embodiment, each $R^6$ is H.

In another preferred embodiment, $A^2$ is

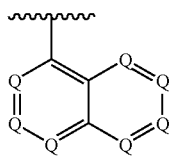

wherein each Q is, independently, C—H, C—$R^5$, C—$R^6$, or a nitrogen atom, with the proviso that at least one Q is nitrogen and one Q is C—$R^5$, and at most three Q in a ring are nitrogen atoms. Therefore, in any one ring, each Q may be 1, 2, or 3 nitrogen atoms. In a preferred embodiment, only one Q in each ring is nitrogen. In another preferred embodiment, only a single Q is nitrogen. Optionally, 1, 2, 3, 4, or 5 Q may be C—$R^6$. Optionally, 1, 2, 3, 4, or 5 Q may be C—H. In a particularly preferred embodiment, each $R^6$ is H.

In another preferred embodiment, $A^2$ is

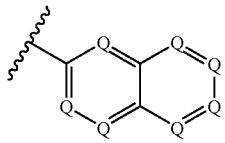

wherein each Q is, independently, C—H, C—$R^5$, C—$R^6$, or a nitrogen atom, with the proviso that at least one Q is nitrogen and one Q is C—$R^5$, and at most three Q in a ring are nitrogen atoms. Therefore, in any one ring, each Q may be 1, 2, or 3 nitrogen atoms. In a preferred embodiment, only one Q in each ring is nitrogen. In another preferred embodiment, only a single Q is nitrogen. Optionally, Q may be 1, 2, 3, 4, or 5 C—H. Optionally, 1, 2, 3, 4, or 5 Q may be C—$R^6$. In a particularly preferred embodiment, each $R^6$ is H.

In a preferred embodiment $R^5$ is one of the following:
—$(CH_2)_m$—$OR^8$, —$(CH_2)_4$—OH, —O—$(CH_2)_m$—$OR^8$, —O—$(CH_2)_4$—OH, —$(CH_2)_n$—$NR^7R^{10}$, —$NHSO_2CH_3$, —$CH_2NH(C=O)$—$(OCH_3)_3$, —$NH(C=O)CH_3$, —$CH_2NH_2$, —NH—$CO_2C_2H_5$, —$CH_2NH(C=O)CH_3$, —$CH_2NHCO_2CH_3$, —$CH_2NHSO_2CH_3$, —$(CH_2)_4$—NH$(C=O)O(CH_3)_3$, —$(CH_2)_4$—$NH_2$, —$(CH_2)_3$—$NH(C=O)O(CH_3)_3$, —$(CH_2)_3$—$NH_2$, —O—$(CH_2)_m$—$NR^7R^{10}$, —$OCH_2CH_2NHCO_2(CH_3)_3$, —$OCH_2CH_2NHCO_2C_2H_5$, —O—$(CH_2)_3$—NH—$CO_2$—$(CH_3)_3$, —O—$(CH_2)_3$—$NH_2$, —$OCH_2CH_2NHSO_2CH_3$, —$(CH_2)_n(CHOR^8)(CHOR^8)_n$—$CH_2OR^8$, —O—$(CH_2)_m(CHOR^8)(CHOR^8)_n$—$CH_2OR^8$, —$OCH_2CHOHCH_2O$-glucuronide, —$OCH_2CH_2CHOHCH_2OH$, —$OCH_2$—(α-CHOH)$_2$CH$_2$OH, —$OCH_2$—$(CHOH)_2CH_2OH$, —$(CH_2CH_2O)_m$—$R^8$, —O—$(CH_2CH_2O)_m$—$R^8$, —$(CH_2CH_2O)_m$—$CH_2CH_2NR^7R^{10}$, —O—$(CH_2CH_2O)_m$—$CH_2CH_2NR^7R^{10}$, —$(CH_2)_n$—$C(=O)NR^7R^{10}$, —$C(=O)NH_2$, —O—$(CH_2)_m$—$C(=O)NR^7R^{10}$, —O—$CH_2$—$(C=O)$NHCH$_2$CHOH, —O—$CH_2$—$(C=O)$NHCH$_2$CHOHCH$_2$OH, —O—$CH_2(C=O)$NHCH$_2$(CHOH)$_2$CH$_2$OH, —O—$CH_2C(C=O)$NHSO$_2$CH$_3$, —O—$CH_2(C=O)$NHCO$_2$CH$_3$, —O—$CH_2$—$C(C=O)$NH—$C(C=O)NH_2$, —O—$CH_2$—$(C=O)$NH—$(C=O)$CH$_3$, —$(CH_2)_n$—$(Z)_g$—$R^7$, —$(CH_2)_n$—(C=N)—$NH_2$, —(C=NH)$NH_2$, —$(CH_2)_n$—NH—C(=NH)—$NH_2$, —$(CH_2)_3$—NH—C(=NH)—$NH_2$, —$CH_2NH$—C(=NH)—$NH_2$, —$(CH_2)_n$—$CONHCH_2(CHOH)_n$—$CH_2OH$, —NH—C(=O)—$CH_2$—$(CHOH)_nCH_2OH$, —NH—(C=O)—NH—$CH_2(CHOH)_2CHOH$, —NHC(C=O)NHCH$_2$CH$_2$OH, —O—$(CH_2)_m$—$(Z)_gR^7$, —O—$(CH_2)_m$—NH—C(=NH)—$N(R^7)_2$, —O(CH$_2$)$_3$—NH—C(=NH)—$NH_2$, —O—$(CH_2)_m$—$CHNH_2$—$CO_2NR^7R^{10}$, —$OCH_2$—$CHNH_2$—$CO_2NH_2$, —O—$(CH_2)_m$—$CHNH_2$—$CO_2NR^7R^{10}$ (anomeric center is the (R) enantiomer), —O—$(CH_2)_m$—$CHNH_2$—$CO_2NR^7R^{10}$ (anomeric center is the (S) enantiomer), —$OCH_2CHOH$—$CH_2NHCO_2(CH_3)_3$, —$(CH_2)_n$—$NR^{10}$—$CH_2(CHOR^8)(CHOR^8)_n$—$CH_2OR^8$, —$NHCH_2(CHOH)_2CH_2OH$, —O—$(CH_2)_m$—$NR^{10}$—$CH_2(CHOR^8)(CHOR^8)_n$—$CH_2OR^8$, —O—$(CH_2)_m$—$CO_2R^7$, —$OCH_2CH_2CO_2(CH_3)_3$, —$OCH_2CO_2H$, —$OCH_2CO_2C_2H_5$, —O—$(CH_2)_m$-Boc, —$(CH_2)_m$-Boc, —O—$(CH_2)_m$—NH—C(=NH)—$N(R^7)_2$, —$(CH_2)_n$—NH—C(=NH)—$N(R^7)_2$, —$(CH_2)_m$—NH—C(=O)—$OR^7$, —O—$(CH_2)_m$—NH—C(=O)—$OR^7$, —$(CH_2)_n$—NH—C(=O)—$R^{11}$, —O—$(CH_2)_m$—NH—C(=O)—$R^{11}$, —O—$(CH_2)_m$—C(=O)N$(R^7)_2$, —$(CH_2)_m$—CHOH—$CH_2$—NH-Boc, —O—$(CH_2)_m$—CHOH—$CH_2$—NHBoc, —$(CH_2)_m$—

NHC(O)OR$^7$, —O—(CH$_2$)$_m$—NHC(O)OR$^7$, —O—(CH$_2$)$_m$—C(=NH)—N(R$^7$)$_2$, or —(CH$_2$)$_n$—C(=NH)—N(R$^7$)$_2$.

In another embodiment, R$^5$ is selected from the group consisting of
—O—(CH$_2$)$_3$—OH, —NH$_2$, —O—CH$_2$—(CHOH)$_2$—CH$_2$OH, —O—CH$_2$—CHOH—CH$_2$OH, —O—CH$_2$CH$_2$—O-tetrahydropyran-2-yl, —O—CH$_2$CHOH—CH$_2$—O-glucuronide, —O—CH$_2$CH$_2$OH, —O—(CH$_2$CH$_2$O)$_4$—CH$_3$, —O—CH$_2$CH$_2$OCH$_3$, —O—CH$_2$—(CHOC(=O)CH$_3$)—CH$_2$—OC(=O)CH$_3$, —O—(CH$_2$CH$_2$O)$_2$—CH$_3$, —OCH$_2$—CHOH—CHOH—CH$_2$OH, —CH$_2$OH, —CO$_2$CH$_3$,

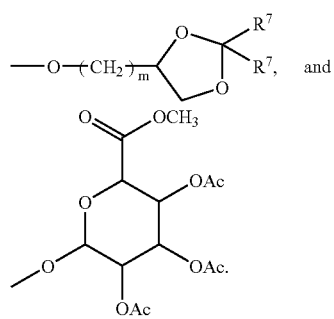

In another embodiment, R$^5$ is selected from the group consisting of —O—(CH$_2$)$_3$—OH, —NH$_2$, —O—CH$_2$—(CHOH)$_2$—CH$_2$OH, —O—CH$_2$—CHOH—CH$_2$OH, —O—CH$_2$CH$_2$—O-tetrahydropyran-2-yl, —O—CH$_2$CHOH—CH$_2$—O-glucuronide, —O—CH$_2$CH$_2$OH, —O—(CH$_2$CH$_2$O)$_4$—CH$_3$, —O—CH$_2$CH$_2$OCH$_3$, —O—CH$_2$—(CHOC(=O)CH$_3$)—CH$_2$—OC(=O)CH$_3$, —O—(CH$_2$CH$_2$O)$_2$—CH$_3$, —OCH$_2$—CHOH—CHOH—CH$_2$OH, —CH$_2$OH, —CO$_2$CH$_3$, —SO$_3$H, —O-glucuronide,

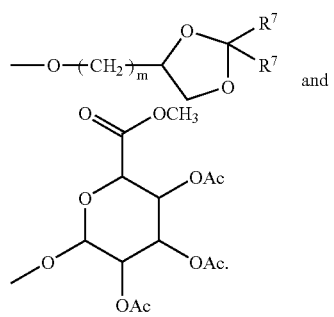

In a preferred embodiment, each —(CH$_2$)$_n$—(Z)$_g$—R$^7$ falls within the scope of the structures described above and is, independently,
—(CH$_2$)$_n$—(C=N)—NH$_2$,
—(CH$_2$)$_n$—NH—C(=NH)NH$_2$,
—(CH$_2$)$_n$—CONHCH$_2$(CHOH)$_n$—CH$_2$OH, or
—NH—C(=O)—CH$_2$—(CHOH)$_n$CH$_2$OH.

In another a preferred embodiment, each —O—(CH$_2$)$_m$—(Z)$_g$—R$^7$ falls within the scope of the structures described above and is, independently,
—O—(CH$_2$)$_m$—NH—C(=NH)—N(R$^7$)$_2$, or
—O—(CH$_2$)$_m$—CHNH$_2$—CO$_2$NR$^7$R$^{10}$.

In another preferred embodiment, R$^5$ may be one of the following: —O—CH$_2$CHOHCH$_2$O-glucuronide, —OCH$_2$CHOHCH$_3$, —OCH$_2$CH$_2$NH$_2$, —OCH$_2$CH$_2$NHCO(CH$_3$)$_3$, —CH$_2$CH$_2$OH, —OCH$_2$CH$_2$OH, —O—(CH$_2$)$_m$-Boc, —(CH$_2$)$_m$-Boc, —OCH$_2$CH$_2$OH, —OCH$_2$CO$_2$H, —O—(CH$_2$)$_m$—NH—C(=NH)—N(R$^7$)$_2$, —(CH$_2$)$_n$—NH—C(=NH)—N(R$^7$)$_2$, —NHCH$_2$(CHOH)$_2$—CH$_2$OH, —OCH$_2$CO$_2$Et, —NHSO$_2$CH$_3$, —(CH$_2$)$_m$—NH—C(=O)—OR$^7$, —O—(CH$_2$)$_m$—NH—C(=O)—OR$^7$, —(CH$_2$)$_n$—NH—C(=O)—R$^{11}$, —O—(CH$_2$)$_m$—NH—C(=O)—R$^{11}$, —O—CH$_2$C(=O)NH$_2$, —CH$_2$NH$_2$, —NHCO$_2$Et, —OCH$_2$CH$_2$CH$_2$OH, —CH$_2$NHSO$_2$CH$_3$, —OCH$_2$CH$_2$CHOHCH$_2$OH, —OCH$_2$CH$_2$NHCO$_2$Et, —NH—C(=NH2)-NH$_2$, —OCH$_2$—(α-CHOH)$_2$—CH$_2$OH, —OCH$_2$CHOHCH$_2$NH$_2$, —(CH$_2$)$_m$—CHOH—CH$_2$—NHBoc, —O—(CH$_2$)$_m$—CHOH—CH$_2$—NHBoc, —(CH$_2$)$_m$—NHC(O)OR$^7$—O—(CH$_2$)$_m$—NHC(O)R$^7$, —OCH$_2$CH$_2$CH$_2$NH$_2$, —OCH$_2$CH$_2$NHCH$_2$(CHOH)$_2$CH$_2$OH, —OCH$_2$CH$_2$NH(CH$_2$[(CHOH)$_2$CH$_2$OH])$_2$, —(CH$_2$)$_4$—NHBoc, —(CH$_2$)$_4$—NH$_2$, —(CH$_2$)$_4$—OH, —OCH$_2$CH$_2$NHSO$_2$CH$_3$, —O—(CH$_2$)$_m$—C(=NH)—N(R$^7$)$_2$, —(CH$_2$)$_n$—C(=NH)—N(R$^7$)$_2$, —(CH$_2$)$_3$—NH Boc, —(CH$_2$)$_3$NH$_2$, —O—(CH$_2$)$_m$—NH—NH—C(=NH)—N(R$^7$)$_2$, —(CH$_2$)$_n$—NH—NH—C(=NH)—N(R$^7$)$_2$, or —O—CH$_2$—CHOH—CH$_2$—NH—C(=NH)—N(R$^7$)$_2$.

In another preferred embodiment, R$^5$ is —OH, —O—(CH$_2$)$_m$(Z)$_g$R$^{12}$, -Het-(CH$_2$)$_m$—NH—C(=NR$^{13}$)—NR$^{13}$R$^{13}$, -Het-(CH$_2$)$_n$—(Z)$_g$—(CH$_2$)$_m$NH—C(=NR$^{13}$)—NR$^{13}$R$^{13}$, -Link-(CH$_2$)$_m$—(Z)$_g$—(CH$_2$)$_m$—CAP, Link-(CH$_2$)$_n$—CR$^{11}$R$^{11}$-CAP, -Het-(CH$_2$)$_m$—CONR$^{13}$R$^{13}$, —(CH$_2$)$_n$—NR$^{12}$R$^{12}$, —O—(CH$_2$)$_m$NR$^{11}$R$^{11}$, —O—(CH$_2$)$_m$—N$^⊕$—(R$^{11}$)$_3$, —(CH$_2$)$_n$—(Z)$_g$—(CH$_2$)$_m$—NR$^{10}$R$^{10}$, -Het-(CH$_2$)$_m$—(Z)$_g$—NH—C(=NR$^{13}$)—NR$^{13}$R$^{13}$, —O—(CH$_2$)$_m$(CHOR$^8$)(CHOR$^8$)$_n$—CH$_2$OR$^8$, —O—(CH$_2$)$_m$—C(=O)NR$^7$R$^{10}$, —O—(CH$_2$)$_m$—(Z)$_g$—R$^7$, or —O—(CH$_2$)$_m$—NR$^{10}$—CH$_2$(CHOR$^8$)(CHOR$^8$)$_n$—CH$_2$OR$^8$.

In a particularly preferred embodiment, R$^5$ is —O—CH$_2$—(CHOH)—CH$_2$OH, —OH, —O—(CH$_2$)$_3$NH$_2$, —O—(CH$_2$)$_3$NH(C=NH)NH$_2$, —O—(CH$_2$)$_2$NH(C=NH)NH$_2$, —O—CH$_2$(CO)NH$_2$, —O—(CH$_2$)$_2$—N$^⊕$—(CH$_3$)$_3$,

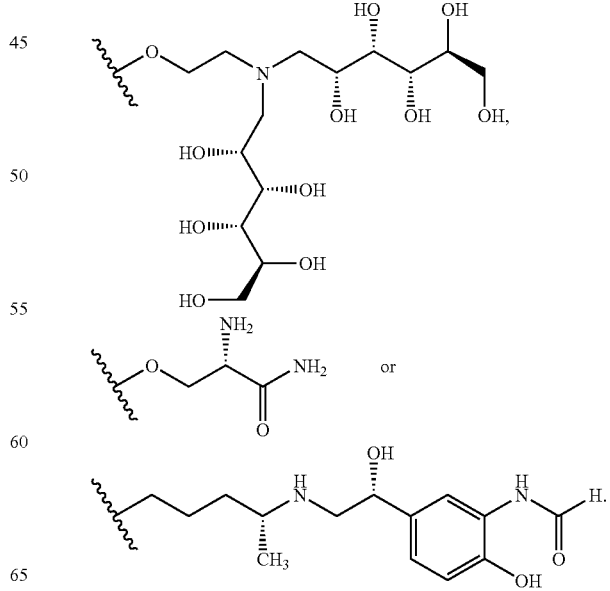

Selected substituents within the compounds of the invention are present to a recursive degree. In this context, "recursive substituent" means that a substituent may recite another instance of itself. Because of the recursive nature of such substituents, theoretically, a large number of compounds may be present in any given embodiment. For example, $R^9$ contains a $R^{13}$ substituent. $R^{13}$ can contain an $R^{10}$ substituent and $R^{10}$ can contain a $R^9$ substituent. One of ordinary skill in the art of medicinal chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis.

By way of example and not limitation, $R^9$, $R^{13}$ and $R^{10}$ are recursive substituents in certain embodiments. Typically, each of these may independently occur 20, 19, 18, 17, 16, 15, 14, 13, 12, 11, 10, 9, 8, 7, 6, 5, 4, 3, 2, 1, or 0, times in a given embodiment. More typically, each of these may independently occur 12 or fewer times in a given embodiment. More typically yet, $R^9$ will occur 0 to 8 times in a given embodiment, $R^{13}$ will occur 0 to 6 times in a given embodiment and $R^{10}$ will occur 0 to 6 times in a given embodiment. Even more typically yet, $R^9$ will occur 0 to 6 times in a given embodiment, $R^{13}$ will occur 0 to 4 times in a given embodiment and $R^{10}$ will occur 0 to 4 times in a given embodiment.

Recursive substituents are an intended aspect of the invention. One of ordinary skill in the art of medicinal chemistry understands the versatility of such substituents. To the degree that recursive substituents are present in an embodiment of the invention, the total number will be determined as set forth above.

Each -Het- is, independently, —N($R^7$)—, —N($R^{10}$)—, —S—, —SO—, —SO$_2$—; —O—, —SO$_2$NH—, —NHSO$_2$—, —NR$^7$CO—, —CONR$^7$—, —N($R^{13}$)—, —SO$_2$NR$^{13}$—, —NR$^{13}$CO—, or —CONR$^{13}$—. In a preferred embodiment, -Het- is —O—, —N($R^7$)—, or —N($R^{10}$)—. Most preferably, -Het- is —O—.

Each -Link- is, independently, —O—, —(CH$_2$)$_n$—, —O(CH$_2$)$_m$—, —NR$^{13}$—C(=O)—NR$^{13}$—, —NR$^{13}$—C(=O)—(CH$_2$)$_m$—, —C(=O)NR$^{13}$—(CH$_2$)$_m^{-1}$, —(CH$_2$)$_n$—(Z)$_g$—(CH$_2$)$_n$—, —S—, —SO—, —SO$_2$—, —SO$_2$NR$^7$—, —SO$_2$NR$^{10}$—, or -Het-. In a preferred embodiment, -Link- is —O—, —(CH$_2$)$_n$—, —NR$^{13}$—C(=O)—(CH$_2$)$_m$—, or —C(=O)NR$^{13}$—(CH$_2$)$_m^-$.

Each -CAP- is, independently, thiazolidinedione, oxazolidinedione, -heteroaryl—C(=O)NR$^{13}$R$^{13}$, heteroaryl-W, —CN, —O—C(=S)NR$^{13}$R$^{13}$, —(Z)$_g$R$^{13}$, —CR$^{10}$((Z)$_g$R$^{13}$)((Z)$_g$R$^{13}$), —C(=O)OAr, —C(=O)NR$^{13}$Ar, imidazoline, tetrazole, tetrazole amide, —SO$_2$NHR$^{13}$, —SO$_2$NH—C(R$^{13}$R$^{13}$)—(Z)$_g$—R$^{13}$, a cyclic sugar or oligosaccharide, a cyclic amino sugar, oligosaccharide, —CR$^{10}$(—(CH$_2$)$_m$—R$^9$)(—(CH$_2$)$_m$—R$^9$), —N(—(CH$_2$)$_m$—R$^9$)(—(CH$_2$)$_m$—R$^9$), —NR$^{13}$(—(CH$_2$)$_m$—CO$_2$R$^{13}$),

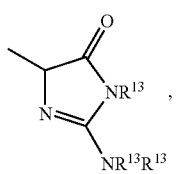 , 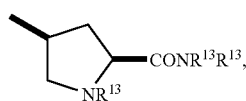

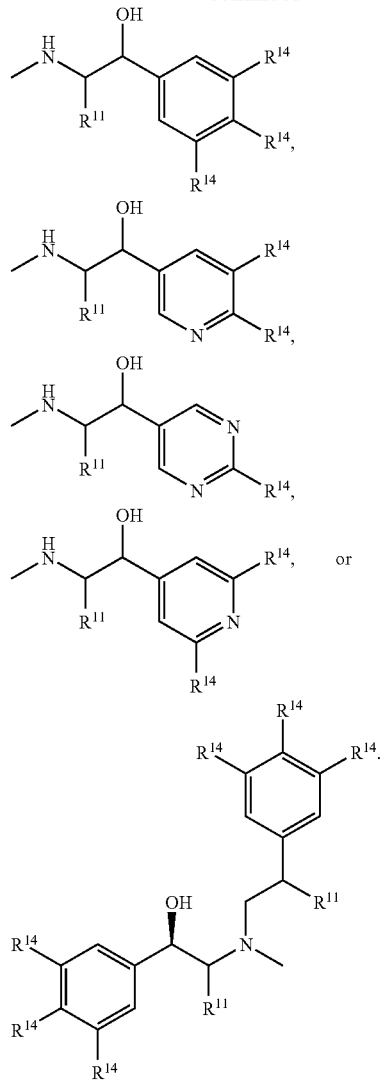

In a preferred embodiment, CAP is

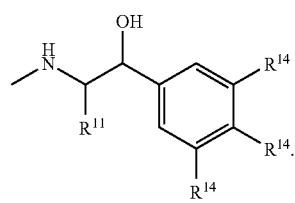

Each Ar is, independently, phenyl, substituted phenyl, wherein the substituents of the substituted phenyl are 1-3 substituents independently selected from the group consisting of OH, OCH$_3$, NR$^{13}$R$^{13}$, Cl, F, and CH$_3$, or heteroaryl.

Examples of heteroaryl include pyridinyl, pyrazinyl, furanyl, thienyl, tetrazolyl, thiazolidinedionyl, imidazoyl, pyrrolyl, quinolinyl, indolyl, adeninyl, pyrazolyl, thiazolyl, isoxazolyl, benzimidazolyl, purinyl, isoquinolinyl, pyridazinyl, pyrimidinyl, 1,2,3-triazinyl, 1,2,4-triazinyl, 1,3,5-triazinyl, cinnolinyl, phthalazinyl, quinazolinyl, quinoxalinyl, and pterdinyl groups.

Each W is, independently, thiazolidinedione, oxazolidinedione, heteroaryl—C(=O)NR$^{13}$R$^{13}$, —CN, —O—C(=S)NR$^{13}$R$^{13}$, —(Z)$_g$R$^{13}$, —CR$^{10}$((Z)$_g$R$^{13}$)((Z)$_g$R$^{13}$), —C(=O)OAr, —C(=O)NR$^{13}$Ar, imidazoline, tetrazole, tetrazole amide, —SO$_2$NHR$^{13}$, —SO$_2$NH—C(R$^{13}$R$^{13}$)—(Z)$_g$—R$^{13}$, a cyclic sugar or oligosaccharide, a cyclic amino sugar, oligosaccharide,

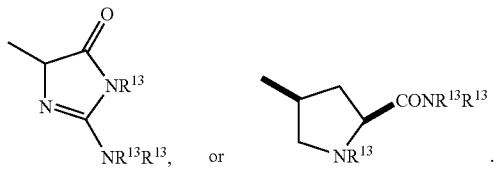

There is at least one R$^5$ on A$^1$ and A$^2$ and the remaining substituents are R$^6$. Each R$^6$ is, independently, R$^5$, —R$^7$, —OR$^{11}$, —N(R$^7$)$_2$, —(CH$_2$)$_m$—OR$^8$, —O—(CH$_2$)$_m$—OR$^8$, —(CH$_2$)$_n$—NR$^7$R$^{10}$, —O—(CH$_2$)$_m$—NR$^7$R$^{10}$, —(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$, —(CH$_2$)$_n$—C(=O)NR$^7$R$^{10}$, —O—(CH$_2$)$_m$—C(=O)NR$^7$R$^{10}$, —(CH$_2$)$_n$—(Z)$_g$—R$^7$, —O—(CH$_2$)$_m$—(Z)$_g$—R$^7$, —(CH$_2$)$_n$—NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$, —OSO$_3$H, —O-glucuronide, —O-glucose,

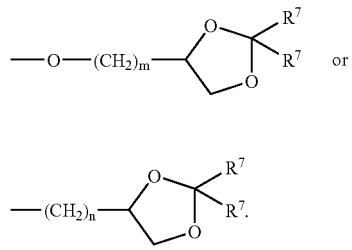

When two R$^6$ are —OR$^{11}$ and are located adjacent to each other on the aromatic carbocycle or aromatic heterocycle, the two OR$^{11}$ may form a methylenedioxy group; i.e., a group of the formula —O—CH$_2$—O—.

In addition, one or more of the R$^6$ groups can be one of the R$^5$ groups which fall within the broad definition of R$^6$ set forth above.

R$^6$ may be hydrogen. Therefore, provided that the aromatic carbocycle or aromatic heterocycle is substituted with R$^5$, the remaining R$^6$ may be hydrogen. Preferably, at most, 3 of the R$^6$ groups are other than hydrogen. More preferably, provided that the aromatic carbocycle or aromatic heterocycle is substituted with R$^5$, then R$^6$ is H.

Each g is, independently, an integer from 1 to 6. Therefore, each g may be 1, 2, 3, 4, 5, or 6.

Each m is an integer from 1 to 7. Therefore, each m may be 1, 2, 3, 4, 5, 6, or 7.

Each n is an integer from 0 to 7. Therefore, each n may be 0, 1, 2, 3, 4, 5, 6, or 7.

Each Z is, independently, —(CHOH)—, —C(=O)—, —(CHNR$^7$R$^{10}$)—, —(C=NR$^{10}$)—, —NR$^{10}$—, —(CH$_2$)$_n$—, —(CHNR$^{13}$R$^{13}$)—, —(C=NR$^{13}$)—, or —NR$^{13}$—. As designated by (Z)$_g$ in certain embodiments, Z may occur one, two, three, four, five or six times and each occurrence of Z is, independently, —(CHOH)—, —C(=O)—, —(CHNR$^7$R$^{10}$)—, —(C=NR$^{10}$)—, —NR$^{10}$—, —(CH$_2$)$_n$—, —(CHNR$^{13}$R$^{13}$)—, —(C=NR$^{13}$)—, or —NR$^{13}$—. Therefore, by way of example and not by way of limitation, (Z)$_g$ can be —(CHOH)—(CHNR$^7$R$^{10}$)—, —(CHOH)—(CHNR$^7$R$^{10}$)—C(=O)—, —(CHOH)—(CHNR$^7$R$^{10}$)—C(=O)—(CH$_2$)$_n$—, —(CHOH)—(CHNR$^7$R$^{10}$)—C(=O)—(CH$_2$)$_n$—(CHNR$^{13}$R$^{13}$)—, —(CHOH)—(CHNR$^7$R')—C(=O)—(CH$_2$)$_n$—(CHNR$^{13}$R$^{13}$)—C(=O)—, and the like.

In any variable containing —CHOR$^8$— or —CH$_2$OR$^8$ groups, when any —CHOR$^8$— or —CH$_2$OR$^8$ groups are located 1,2- or 1,3- with respect to each other, the R$^8$ groups may, optionally, be taken together to form a cyclic mono- or di-substituted 1,3-dioxane or 1,3-dioxolane.

More specific examples of suitable compounds represented by formula (I) are shown in formulas II and III below wherein A$^1$ and A$^2$ are defined as above:

formula II

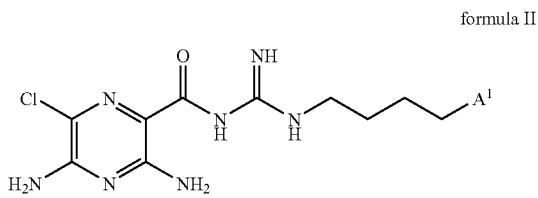

formula III

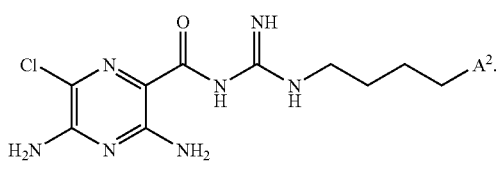

In a preferred aspect of formula II, A$^1$ is selected from indenyl, napthalenyl, 1,2-dihydronapthalenyl, 1,2,3,4-tetrahydronapthalenyl, anthracenyl, fluorenyl, phenanthrenyl, azulenyl, cyclohepta-1,3,5-trienyl or 5H-dibenzo[a,d]cycloheptenyl.

In another preferred aspect of formula II, A$^1$ is

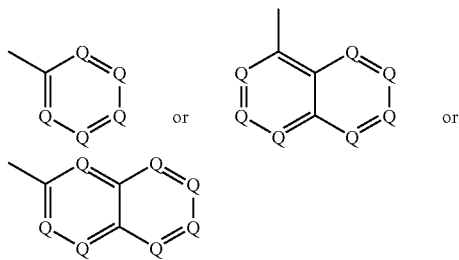

More preferably, R$^5$ is —O—CH$_2$—(CHOH)—CH$_2$OH, —OH, —O—(CH$_2$)$_3$NH$_2$, —O—(CH$_2$)$_3$NH(C=NH)NH$_2$, —O—(CH$_2$)$_2$NH(C=NH)NH$_2$, —O—CH$_2$(CO)NH$_2$, —O—(CH$_2$)$_2$—N$^\oplus$—(CH$_3$)$_3$,

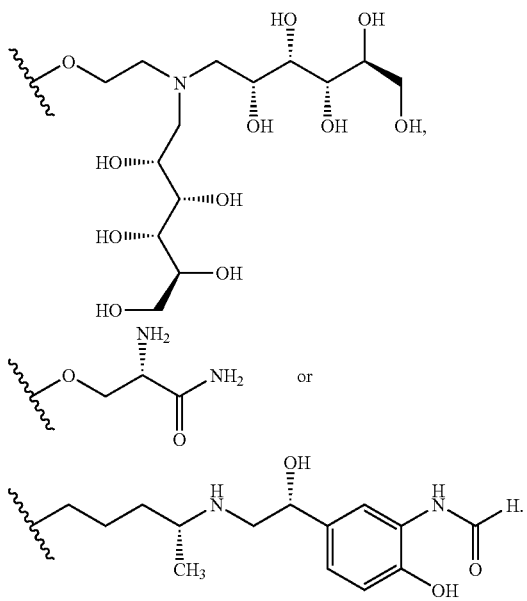

Most preferably, R⁵—O—CH₂—(CHOH)—CH₂OH, —OH, —O—(CH₂)₃NH₂, —O—(CH₂)₃NH(C=NH)NH₂, —O—(CH₂)₂NH(C=NH)NH₂, —O—CH₂(CO)NH₂, —O—(CH₂)₂—N⊕—(CH₃)₃,

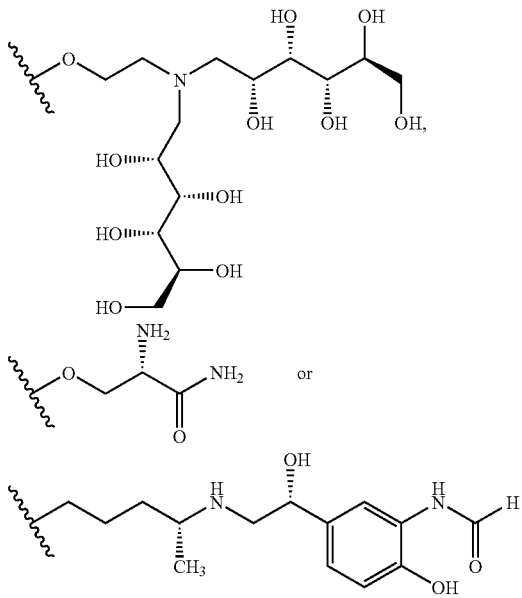

and six Q are C—H.
In another preferred aspect of formula II, A¹ is

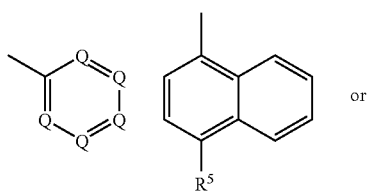

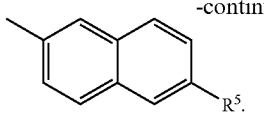

Preferably, R⁵ is —OH, —O—(CH₂)ₘ(Z)ₘR¹², -Het-(CH₂)ₘ—NH—C(=NR¹³)—NR¹³R¹³, -Het-(CH₂)ₙ—(Z)ₘ—(CH₂)ₘNH—C(=NR¹³)—NR¹³R¹³, -Link-(CH₂)ₘ—(Z)ₘ—(CH₂)ₘ—CAP, Link-(CH₂)ₙ—CR¹¹R¹¹-CAP, -Het-(CH₂)ₘ—CONR¹³R¹³, —(CH₂)ₙ—NR¹²R¹², —O—(CH₂)ₘNR¹¹R¹¹, —O—(CH₂)ₘ—N⊕—(R¹¹)₃, —(CH₂)ₙ—(Z)ₘ—(CH₂)ₘ—NR¹⁰R¹⁰, -Het-(CH₂)ₘ—(Z)ₘ—NH—C(=NR¹³)—NR¹³R¹³, —O—(CH₂)ₘ(CHOR⁸)(CHOR⁸)ₙ—CH₂OR⁸, —O—(CH₂)ₘ—C(=O)NR⁷R¹⁰, —O—(CH₂)ₘ—(Z)ₘ—R⁷, or —O—(CH₂)ₘ—NR¹⁰—CH₂(CHOR⁸)(CHOR⁸)ₙ—CH₂OR⁸. Most preferably, R⁵ is —O—CH₂—(CHOH)—CH₂OH, —OH, —O—(CH₂)₃NH₂, —O—(CH₂)₃NH(C=NH)NH₂, —O—(CH₂)₂NH(C=NH)NH₂, —O—CH₂(CO)NH₂, —O—(CH₂)₂—N⊕—(CH₃)₃,

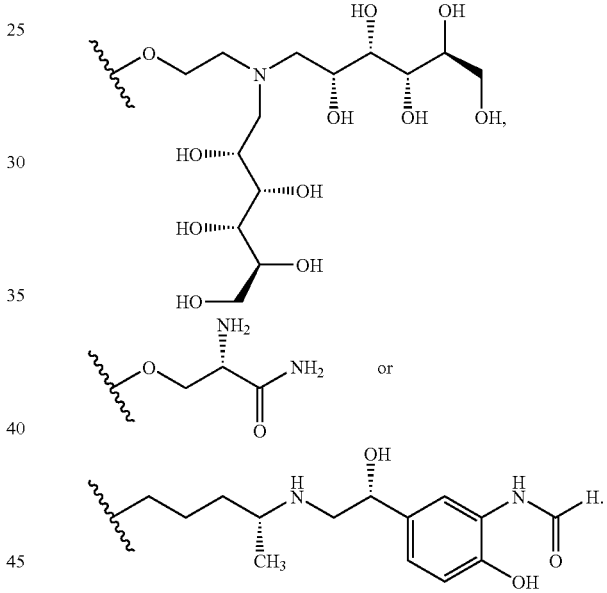

In a preferred aspect of formula III, A² is selected from pyridyl, indolizinyl, indolyl, isoindolyl, indolinyl, benzo[b]furanyl, 2,3-dihydrobenzo[b]furanyl, benzo[b]thiophenyl, 2,3-dihydrobenzo[b]thiophenyl, indazolyl, benzimidazolyl, benzthiazolyl, purinyl, quinolinyl, 1,2,3,4-tetrahydroquinolinyl, 3,4-dihydro-2H-chromenyl, 3,4-dihydro-2H-thiochromenyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, dibenzofuranyl, dibenzothiophenyl, 1H-azepinyl, 5H-dibenz[b,f]azepinyl, or 10,11-dihydro-5H-dibenz[b,f]azepinyl.

In another preferred aspect of formula III, A² is

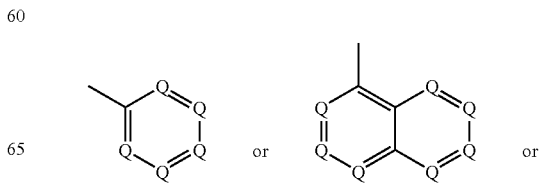

-continued

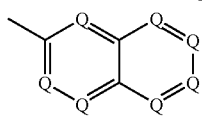

wherein each Q is, independently, C—H, C—$R^5$, C—$R^6$, or a nitrogen atom, with the proviso that at least one Q is nitrogen and one Q is C—$R^5$, and at most three Q in a ring are nitrogen atoms. In a preferred embodiment, only one Q in each ring is nitrogen. In another preferred embodiment, only a single Q is nitrogen. In a particularly preferred embodiment, a single Q is nitrogen, one Q is C—$R^5$, and the remaining Q are C—H. In another preferred embodiment, each $R^6$ is H. Preferably, $R^5$ is —OH, —O—$(CH_2)_m(Z)_g R^{12}$, -Het-$(CH_2)_m$—NH—C(=$NR^{13}$)—$NR^{13}R^{13}$, -Het-$(CH_2)_n$—$(Z)_g$—$(CH_2)_m$NH—C(=$NR^{13}$)—$NR^{13}R^{13}$, -Link-$(CH_2)_m$—$(Z)_g$—$(CH_2)_m$—CAP, Link-$(CH_2)_n$—$CR^{11}R^{11}$-CAP, -Het-$(CH_2)_m$—$CONR^{13}R^{13}$, —$(CH_2)_n$—$NR^{13}R^{13}$, —O—$(CH_2)_m NR^{11}R^{11}$, —O—$(CH_2)_m$—$N^{\oplus}(R^{11})_3$, —$(CH_2)_n$—$(Z)_g$—$(CH_2)_m$—$NR^{10}R^{10}$, -Het-$(CH_2)_m$—$(Z)_g$—NH—C(=$NR^{13}$)—$NR^{13}R^{13}$, —O—$(CH_2)_m(CHOR^8)(CHOR^8)_n$—$CH_2OR^8$, —O—$(CH_2)_m$—C(=O)$NR^7R^{10}$, —O—$(CH_2)_m$—$(Z)_g$—$R^7$, or —O—$(CH_2)_m$—$NR^{10}$—$CH_2(CHOR^8)(CHOR^8)_n$—$CH_2OR^8$. More preferably, one Q is nitrogen, five Q are C—H and $R^5$ is —OH, —O—$(CH_2)_m(Z)_g R^{12}$, -Het-$(CH_2)_m$—NH—C(=$NR^{13}$)—$NR^{13}R^{13}$, -Het-$(CH_2)_n$—$(Z)_g$—$(CH_2)_m$NH—C(=$NR^{13}$)—$NR^{13}R^{13}$, -Link-$(CH_2)_n$—$(Z)_g$—$(CH_2)_m$—CAP, Link-$(CH_2)_n$—$CR^{11}R^{11}$-CAP, -Het-$(CH_2)_m$—$CONR^{13}R^{13}$, —$(CH_2)_n$—$NR^{12}R^{12}$, —O—$(CH_2)_m NR^{11}R^{11}$, —O—$(CH_2)_m$—$N^{\oplus}(R^{11})_3$, —$(CH_2)_n$—$(Z)_g$—$(CH_2)_m$—$NR^{10}R^{10}$, -Het-$(CH_2)_m$—$(Z)_g$—NH—C(=$NR^{13}$)—$NR^{13}R^{13}$, —O—$(CH_2)_m(CHOR^8)(CHOR^8)_n$—$CH_2OR^8$, —O—$(CH_2)_m$—C(=O)$NR^7R^{10}$, —O—$(CH_2)_m$—$(Z)_g$—$R^7$, or —O—$(CH_2)_m$—$NR^{10}$—$CH_2(CHOR^8)(CHOR^8)_n$—$CH_2OR^8$. More preferably, $R^5$ is —O—$CH_2$—(CHOH)—$CH_2OH$, —OH, —O—$(CH_2)_3NH_2$, —O—$(CH_2)_3NH(C=NH)NH_2$, —O—$(CH_2)_2NH(C=NH)NH_2$, —O—$CH_2(CO)NH_2$, —O—$(CH_2)_2$—$N^{\oplus}$—$(CH_3)_3$,

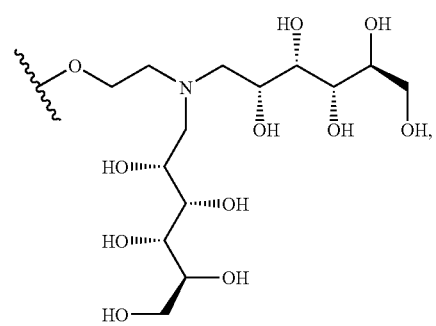

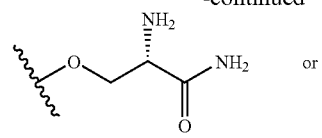

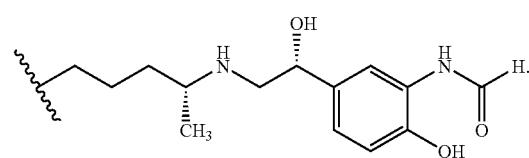

Most preferably, $R^5$ is —O—$CH_2$—(CHOH)—$CH_2OH$, —OH, —O—$(CH_2)_3NH_2$, —O—$(CH_2)_3NH(C=NH)NH_2$, —O—$(CH_2)_2NH(C=NH)NH_2$, —O—$CH_2(CO)NH_2$, —O—$(CH_2)_2$—$N^{\oplus}$—$(CH_3)_3$,

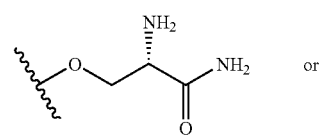

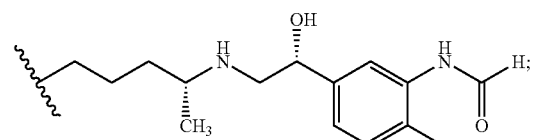

a single Q is nitrogen and five Q are C—H.

In a particularly preferred embodiment, the compounds of formula I, formula II, or formula III are:

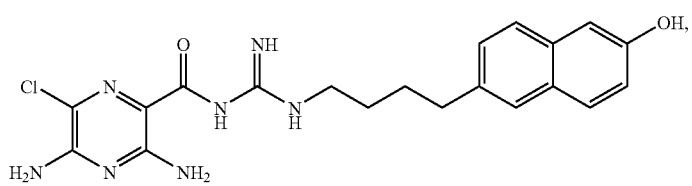

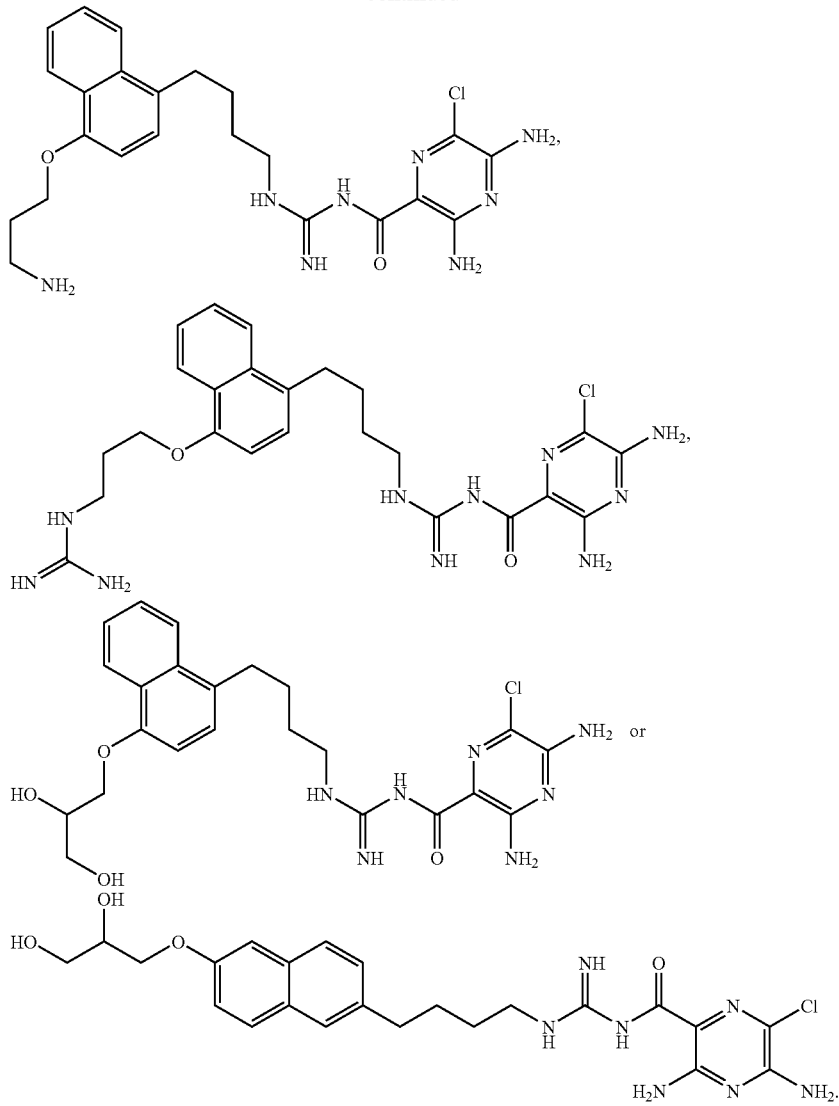

The compounds described herein may be prepared and used as the free base. Alternatively, the compounds may be prepared and used as a pharmaceutically acceptable salt. Pharmaceutically acceptable salts are salts that retain or enhance the desired biological activity of the parent compound and do not impart undesired toxicological effects. Examples of such salts are (a) acid addition salts formed with inorganic acids, for example, hydrochloric acid, hydrobromic acid, sulfuric acid, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid and the like; and (c) salts formed from elemental anions for example, chlorine, bromine, and iodine.

It is to be noted that all enantiomers, diastereomers, and racemic mixtures, tautomers, polymorphs, pseudopolymorphs and pharmaceutically acceptable salts of compounds within the scope of formula (I), formula II, or formula III are embraced by the present invention. All mixtures of such enantiomers and diastereomers are within the scope of the present invention.

A compound of formula I-III and its pharmaceutically acceptable salts may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of formula I-III and their pharmaceutically acceptable salts.

A compound of formula I-III and its pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of formula I-III and their pharmaceutically acceptable salts.

The compounds of formula I-III may exist in different tautomeric forms. One skilled in the art will recognize that amidines, amides, guanidines, ureas, thioureas, heterocycles and the like can exist in tautomeric forms. By way of example and not by way of limitation, compounds of formula I-III can exist in various tautomeric forms as shown below:

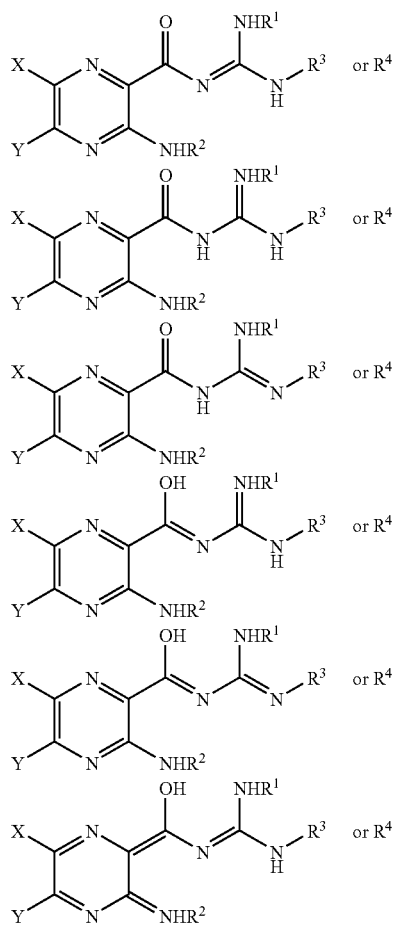

All possible tautomeric forms of the amidines, amides, guanidines, ureas, thioureas, heterocycles and the like of all of the embodiments of formula I-III are within the scope of the instant invention.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l, D and L, or (+) and (−) are employed to designate the sign of rotation of plane-polarized light by the compound, with S, (−), or l meaning that the compound is levorotatory while a compound prefixed with R, (+), or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

A single stereoisomer, e.g. an enantiomer, substantially free of its stereoisomer may be obtained by resolution of the racemic mixture using a method such as formation of diastereomers using optically active resolving agents ("Stereochemistry of Carbon Compounds," (1962) by E. L. Eliel, McGraw Hill; Lochmuller, C. H., (1975) *J. Chromatogr.*, 113:(3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

It is to be noted that all enantiomers, diastereomers, and racemic mixtures of compounds within the scope of formula (I) are embraced by the present invention. All mixtures of such enantiomers and diastereomers are within the scope of the present invention.

In another preferred embodiment of the present invention, the compound of Formula I is represented by the formula:

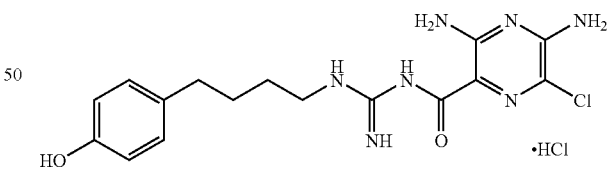

In another preferred embodiment of the present invention, the compound of Formula I is represented by the formula:

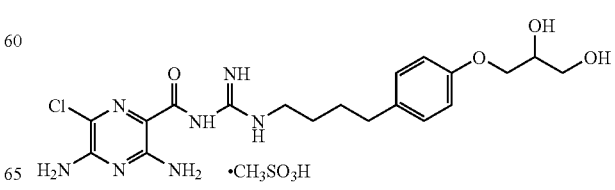

In another preferred embodiment of the present invention, the compound of Formula I is represented by the formula:

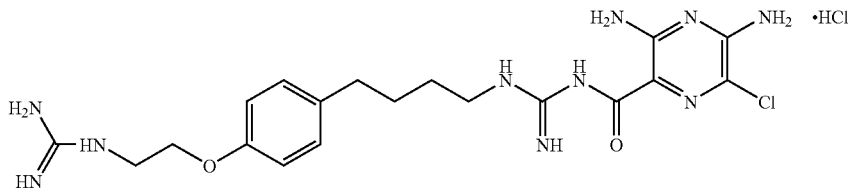

In another preferred embodiment of the present invention, the compound of Formula I is represented by the formula:

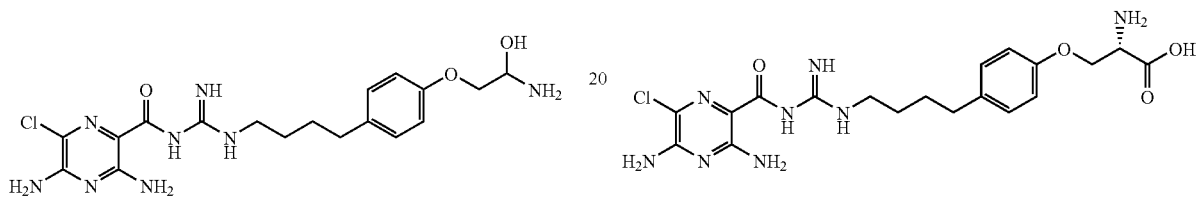

In another preferred embodiment of the present invention, the compound of Formula I is represented by the formula:

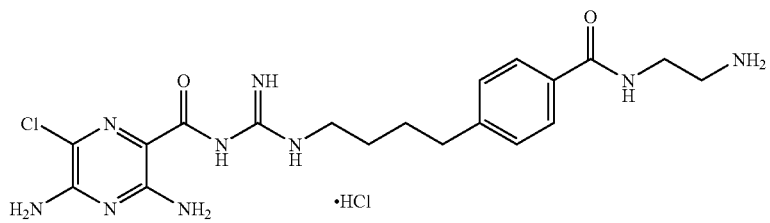

In another preferred embodiment of the present invention, the compound of Formula I is represented by the formula:

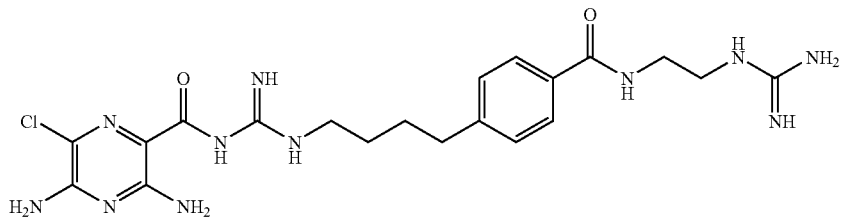

In another preferred embodiment of the present invention, the compound of Formula I is represented by the formula:

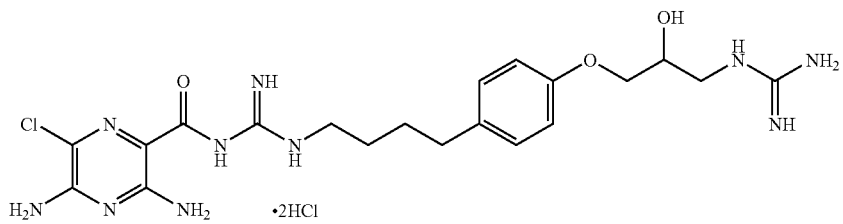

In another preferred embodiment of the present invention, the compound of Formula I is represented by the formula:

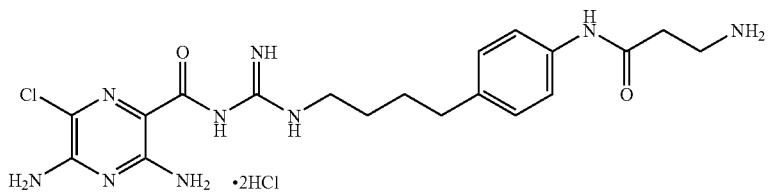

The compounds of formula (I) may be prepared and used as the free base or zwiterion. Alternatively, the compounds may be prepared and used as a pharmaceutically acceptable salt. Pharmaceutically acceptable salts are salts that retain or enhance the desired biological activity of the parent compound and do not impart undesired toxicological effects. Examples of such salts are (a) acid addition salts formed with inorganic acids, for example, hydrochloric acid, hydrobromic acid, sulfuric acid, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid and the like; and (c) salts formed from elemental anions for example, chlorine, bromine, and iodine.

It is to be noted that all enantiomers, diastereomers, and racemic mixtures of compounds within the scope of formula (I) are embraced by the present invention. All mixtures of such enantiomers and diastereomers are within the scope of the present invention. The above compounds can be a pharmaceutically acceptable salt thereof, and wherein the above compounds are inclusive of all racemates, enantiomers, diastereomers, tautomers, polymorphs and pseudopolymorphs thereof.

Without being limited to any particular theory, it is believed that the compounds of formula (I) function in vivo as sodium channel blockers and ASIC Blockers.

The present invention is concerned primarily with the modification of taste in human subjects, but may also be employed for the treatment of other mammalian subjects, such as dogs and cats, for veterinary purposes.

As discussed above, the compounds used to prepare the compositions of the present invention may be in the form of a pharmaceutically acceptable free base.

Another aspect of the present invention is a pharmaceutical formulation, comprising an active compound as described above in a pharmaceutically acceptable carrier (e.g., an aqueous carrier solution). In general, the active compound is included in the composition in an amount effective to block sodium channels.

The active compounds disclosed herein may be administered to oral cavity mucosal surfaces by any suitable means, including topically and orally, as desired.

The compounds of formula (I) may be synthesized according to procedures known in the art. A representative synthetic procedure is shown in the scheme below:

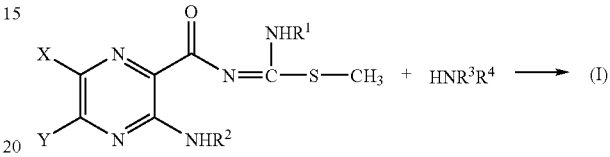

These procedures are also described in, for example, E. J. Cragoe, "The Synthesis of Amiloride and Its Analogs" (Chapter 3) in Amiloride and Its Analogs, pp. 25-36, incorporated herein by reference. Other methods of preparing the compounds are described in, for example, U.S. Pat. No. 3,313,813, incorporated herein by reference. See in particular Methods A, B, C, and D described in U.S. Pat. No. 3,313,813.

Several assays may be used to characterize the ENaC and ASICs properties of the compounds of Formula I as defined herein of the present invention. Representative assays are discussed below.

ENaC Potentcy: In Vitro Measure of Sodium Channel Blocking Activity and Reversibility One assay used to assess mechanism of action and/or potency of the compounds of the present invention involves the determination of lumenal drug inhibition of airway epithelial sodium currents measured under short circuit current ($I_{SC}$) using airway epithelial monolayers mounted in Ussing chambers. Cells obtained from freshly excised human, dog or sheep airways are seeded onto porous 0.4 micron Snapwell™ Inserts (CoStar), cultured at air-liquid interface (ALI) conditions in hormonally defined media, and assayed for sodium transport activity ($I_{SC}$ in $\mu A/cm^2$) while bathed in Krebs Bicarbonate Ringer (KBR) in Ussing chambers. All test drug additions are to the lumenal bath with half-log dose addition protocols (from $1 \times 10^{-11}$ M to $3 \times 10^{-5}$ M), and the cumulative change in $I_{SC}$ (inhibition) recorded. All drugs are prepared in dimethyl sulfoxide as stock solutions at a concentration of $1 \times 10^{-2}$ M and stored at $-20°$ C. Six preparations are typically run in parallel; one preparation per run incorporates a positive control. All data from the voltage clamps are collected via a computer interface and analyzed off-line.

Dose-effect relationships for all compounds are considered and analyzed by the Prism 3.0 program. $EC_{50}$ values, maximal effective concentrations are calculated and compared to positive controls.

ASIC Potentcy: In Vitro Measure of ASIC Blocking Activity

A method for measuring potency of ASIC blockers is by using an automated patch-clamping apparatus, the QPatch 16 (Sophion, Denmark). The QPatch 16 uses four pipette heads that afford more efficient assays and faster throughput for ion channel drug discovery. The QPlate contains 16 individual patch-clamp sites that are operated asynchronously and in parallel. Ringer's solutions and compounds are applied by four pipettes. HEK-293 cells expressing ASIC ion channels are kept in culture medium in the stirred reservoir for up to four hours. Prior to testing, the cells are transferred to an on-board mini centrifuge, spun down and washed in Ringer's solution twice before being applied to the pipetting wells in the QPlate. Gigaseals are formed upon execution of a combined suction/voltage protocol. Further suction lead to whole-cell configuration. Solutions and compounds were applied through the glass flow channels in the QPlate. All currents are recorded at a patch potential of −70 mV. Liquid flow was laminar with exchange time constants in of 50-100 ms.

Pharmacological Assays of Absorption: In Vitro Mucosal Retention Assay

Human tracheobronchial cells or buccal epithelial cells purchased from Mattek Corp. seeded on porous Millipore Millicell™ CM single well tissue culture plate inserts Pore size=0.4 µm, Surface area=4.2 cm$^2$ grown at an air-liquid interface in hormonally defined media that promotes a polarized epithelium are tested for apparent permeability. From 6 to 25 days after development of an air-liquid interface (ALI) tracheobrochial cultures are expected to be >90% ciliated, and mucins will accumulate on the cells. To ensure the integrity of epithelial cell preparation, the transepithelial resistance ($R_t$) and transepithelial potential differences (PD), which are indicators of the integrity of polarized nature of the culture, are measured. The permeability assay is initiated by adding novel chemical entities or positive controls to the apical surface at a selected concentration ranging from 1-100 µM. A series of samples (5-500 µl volume per sample depending on compartment sampled and method used) is collected at various time points, from both the apical and serosal bath. Concentrations are determined by measuring intrinsic fluorescence of each compound using HPLC. Quantitative analysis employs a standard curve generated from authentic reference standard materials of known concentration and purity. Data analysis calculating the apparent permeability coefficient, and both the rate of apical disappearance and serosal appearance, is performed using nonlinear regression analysis software used is GraphPad Prism V4.0.

The invention claimed is:

1. A method of blocking salt taste, comprising administering to a subject an effective amount of a compound represented by the formula:

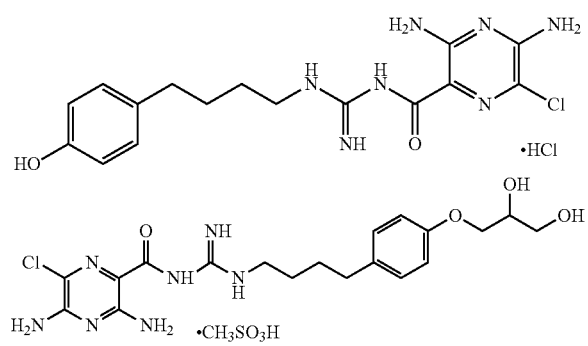

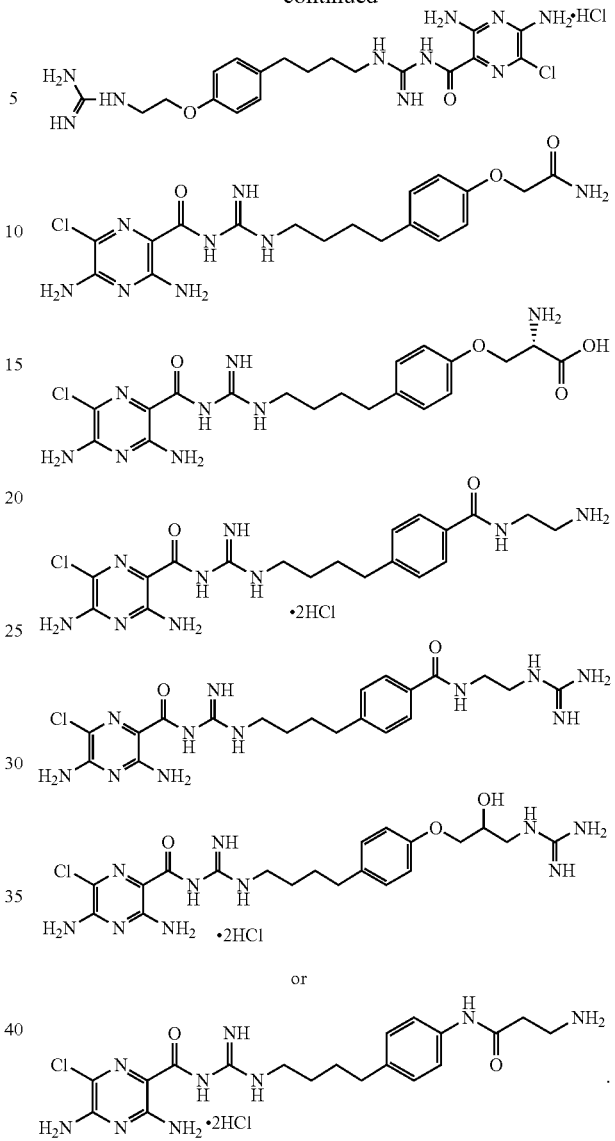

2. The method of claim 1, wherein the compound is:

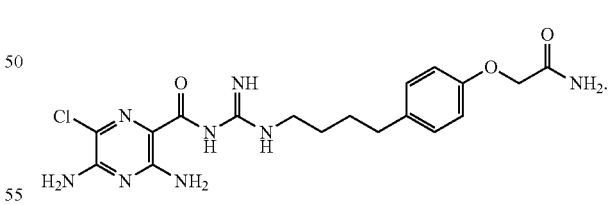

3. The method of claim 1, wherein the compound is administered topically.

4. The method of claim 1, wherein the compound is administered orally.

* * * * *